US007732578B2

(12) United States Patent
Foote

(10) Patent No.: US 7,732,578 B2
(45) Date of Patent: Jun. 8, 2010

(54) SUPER HUMANIZED ANTIBODIES

(75) Inventor: Jefferson Foote, Seattle, WA (US)

(73) Assignee: Arrowsmith Technology Licensing LLC, Seattle, WA (US)

( * ) Notice: Subject to any disclaimer, the term of this patent is extended or adjusted under 35 U.S.C. 154(b) by 340 days.

(21) Appl. No.: 11/054,669

(22) Filed: Feb. 8, 2005

(65) Prior Publication Data
US 2005/0261480 A1 Nov. 24, 2005

Related U.S. Application Data

(62) Division of application No. 10/194,975, filed on Jul. 12, 2002, now Pat. No. 6,881,557.

(60) Provisional application No. 60/305,111, filed on Jul. 12, 2001.

(51) Int. Cl.
*C07K 16/00* (2006.01)
*A61K 39/395* (2006.01)
*C12P 21/04* (2006.01)
*C12P 21/06* (2006.01)
*C12N 5/06* (2006.01)
*C07H 21/04* (2006.01)

(52) U.S. Cl. ............... 530/387.3; 424/133.1; 424/141.1; 424/154.1; 424/156.1; 435/69.1; 435/69.6; 435/326; 435/328; 530/387.1; 530/388.1; 530/388.75; 530/388.85

(58) Field of Classification Search ........................ None
See application file for complete search history.

(56) References Cited

U.S. PATENT DOCUMENTS

| | | | |
|---|---|---|---|
| 5,225,539 | A | 7/1993 | Winter |
| 5,530,101 | A * | 6/1996 | Queen et al. |
| 5,693,761 | A | 12/1997 | Queen et al. |
| 5,821,337 | A | 10/1998 | Carter et al. |
| 5,859,205 | A | 1/1999 | Adair et al. |
| 5,869,619 | A | 2/1999 | Studnicka |
| 6,479,284 | B1 | 11/2002 | Marasco et al. |

FOREIGN PATENT DOCUMENTS

FR 2724393 A1 * 3/1996

OTHER PUBLICATIONS

Fundamental Immunology, William E. Paul, ed., 3rd Ed., pp. 292-295, 1993.*
Rudikoff et al. Proc. Natl. Acad. Sci. USA, 79:1979-1983, Mar. 1982.*
Colman P. M. Research in Immunology, 145:33-36, 1994.*
Bendig M. M. Methods: A Companion to Methods in Enzymology, 8:83-93, 1995.*
MacCallum et al. J. Mol. Biol., 262, 732-745, 1996.*
Casset et al. Biochemical and Biophysical Research Communications, 307:198-205, 2003.*
Holmes et al. The Journal of Immunology, 158:2192-2201, 1997.*
Hwang et al. Methods, 36:35-42, 2005.*
Takemura et al. FEBS Letters, 476(3):266-271, Jul. 7, 2000.*
Routledge et al (1993) (Protein Engineering of Antibody Molecules for Prophylactic and Therapeutic Applications in Man (Clark, M., ed), pp. 14-44, Academic Titles, Nottingham, UK.*
Carter, P. et al., "High Level *Escheria coli* Expression and Production of a Bivalent Humanized Antibody Fragment" *Bio/Technology* (Feb. 1992), vol. 10, pp. 163-167.
Chomecznski et al., "Single Step Method of RNA Isolation by Acid Guanidinium Thiocynate-Phenol_Chloroform Extraction", *Anal. Biochem* (1987), vol. 162, pp. 156-159.
Chothia et al. "Canonical Structures for the Hypervariable Regions of Immunoglobulins", *J. Mol. Biol.* (1987), vol. 196, pp. 901-917.
Chothia et al., "Structural Repertoire of the Human VH Segments", *J. Mol. Biol.* (1992), vol. 227, pp. 799-817.
Foote J. et al., "Antibody Residues Affecting Conformation of the Hypervariable Loops", *J. Mol. Biol.* (1992), vol. 224, pp. 487-499.
Hampe et al. "A Novel Monoclonal Antibody Specific for the N-Terminal End of GAD65", *J. Neuroimmunol.* (2001), vol. 113, pp. 63-71.
Hansen, J.A. et al., "Monoclonal Antibodies Identifying a Novel T Cell Antigen and Ia Antigens of Human Lymphocytes", *Immunogenetics* (1980), vol. 10, pp. 247-260.
Henikoff S. et al., "Amino Acid Substitution Matrices from Protein Blocks", *Proc. Natl. Acad. Sci. USA* (Nov. 1992), vol. 89, pp. 10915-10919.
Jin., L. et al., "High Resolution Functional Analysis of Antibody-Antigen Interactions", *J. Mol. Biol. 1992*), vol. 226, pp. 851-865.
Jones, P.T. et al., "Replacing the Complementarity-Determining Regions in a Human Antibody with Those from a Mouse", *Nature* (1986), vol. 321, pp. 522-525.

(Continued)

*Primary Examiner*—David J. Blanchard
(74) *Attorney, Agent, or Firm*—Townsend and Townsend and Crew LLP

(57) ABSTRACT

Disclosed herein are methods for humanizing antibodies based on selecting variable region framework sequences from human antibody genes by comparing canonical CDR structure types for CDR sequences of the variable region of a non-human antibody to canonical CDR structure types for corresponding CDRs from a library of human antibody sequences, preferably germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. Top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

12 Claims, 15 Drawing Sheets

OTHER PUBLICATIONS

Jönsson, U. et al. "Real-time Biospecific Interaction Analysis Using Surface Plasmon Resonance and a Sensor Chip Technology", *BioTechniques* (1991), vol. 11, pp. 620-627.

Kabat, et al., *Sequences of Proteins of Immunological Interest*, 5th ed. 1991, Bethesda: US Dept. of Health and Human Services, PHS, NIH.

Licea, A.F. et al., "Fab Fragments of the Monoclonal Antibody BCF2 are Capable of Neutralizing the Whole Soluble Venom from the Scorpion *Centruoides noxius*", *Toxicon* (1996), vol. 34, No. 8, pp. 843-847.

MacCallum, R.M et al., "Antibody-Antigen Interactions: Contact Analysis and Binding Site Topography", *J. Mol. Biol.* (1996), vol. 262, pp. 732-745.

Martin, A.C.R. et al., "Structural Families in Loops of Homologous Proteins: Automatic Classification, Modelling and Application to Antibodies," *J. Mol. Biol.* (1996), vol. 263, pp. 800-815.

Padlan, E.O et al., "Identification of Specifity-Determining Residues in Antibodies," *FASEB J.*(1995), vol. 332, No. 6162, 9, 133-139.

Padlan, E.A., "A Possible Procedure for Reducing the Immunogencity of Antibody Variable Domains while Preserving their Ligand-Binding Properties" *Mol. Immunol.* (1991), voil. 28, No. 4, pp. 489-498.

Riechmann, et al., "Reshaping Human Antibodies forTherapy", *Nature* (1988), vol. 332, pp. 323-327.

Rutgeerts, P. et al., "Efficacy and Safety of Retreatment with Anti-Tumor Necrosis Factor Antibody (Infliximab) to Maintain Remission in Crohn's Disease," *Gastroenterology* (1999), vol. 117, pp. 761-769.

Selisko, B., et al., "Antibody BCF2 S Against Scorpion Toxin Cn2 from *Centruoides noxius* Hoffman: Primary Structure and Three-Dimensional Model as Free Fv Fragment and Complexed with its Antigen," *Proteins: Structure, Function and Genetics* (1999), vol. 37, pp. 130-143.

Tamura, M. et al., "Structural Correlates of an Anticarcinoma Antibody: Identification of Specificty -Determining Residues (SDRs) and Development of a Minimally Immunogenic Antibody Variant by Rentention of SDRs only", *J. Immunol.* (2000), vol. 164, pp. 1432-1441.

Tomlinson, I.M. et al., "The Structural Repertoire of the Human Vk Domain", *EMBO J.* (1995), vol. 14, No. 18, pp. 4628-4638.

Wu, T.T., et al., "An Analysis if the Sequences of the Variable Regions of Bence Jones Proteins and Myeloma Light Chains and their Implications for Antibody Complentariity" *J. Exp. Med.* (1970), vol. 132, pp. 211-250.

Ye, Q, et al., "Gene Synthesis and Expression in *E. coli* for Pump, a Human Matrix Metalloproteinase", *Biochem, Biophys. Res. Comm.* (1992), vol. 186, No. 1, pp. 143-149.

Holmes, M. et al. "Structural effects of framework mutation on a humanized anti-lysozyme antibody" *Journal of Immunology* (2001) 167(1): 296-301.

Morea, V. et al. "Antibody Modeling: Implication for Engineering and Design" *Methods: A Companion to Methods in Enzymology* (2000) 20(3):267-279.

Tan, P. et al. "Superhumanized Antibodies: Reduction of Immunogenic Potential by Complementarity-Determining Region Grafting with Human Germline Sequences: Application to an Anti-CD28" Journal of Immunology (2002) 169(2):1119-1125.

Alberts et al., *Molecular Biology of the Cell*, 3rd Edition, pp. 1216-1218, 1994.

Carter et al., "Humanization of an Anti-p185HER2 Antibody for Human Cancer Therapy." *Proc. Natl. Acad. Sci. USA*, vol. 89, pp. 4285-4289, May 1992.

Iwahashi et al., "CDR Substitutions of a Humanized Monoclonal Antibody (CC49): Contributions of Individual CDRs to Antigen Binding and Immunogenicity." *Molecular Immunology*, vol. 36, pp. 1079-1091, 1999.

Lewin et al., *Genes IV*, p. 810, Oxford University Press, 1990.

Mhashilkar et al., "Inhibition of Human Immunodeficiency Virus Type 1 Replication in Vitro in Acutely and Persistently Infected Human CD4+ Mononuclear Cells Expressing Murine and Humanized Anti-Human Immunodeficiency Virus Type 1 Tat Single-Chain Variable Fragment Intrabodies." *Human Gene Therapy*, vol. 10, pp. 1453-1467, 1999.

Presta et al., "Humanization of an Antibody Directed Against IgE." *The Journal of Immunology*, vol. 151, No. 5, pp. 2623-2632, Sep. 1, 1993.

Riechmann et al., "Single Domain Antibodies: Comparison of Camel VH and Camelised Human VH Domains." *Journal of Immunological Methods*, vol. 231, pp. 25-38, 1999.

Rosok et al., "A Combinatorial Library Strategy for the Rapid Humanization of Anticarcinoma BR96 Fab." *J. Biol. Chem.*, vol. 271, No. 37, pp. 22611-22618, 1996.

U.S. Appl. No. 60/305,111, filed Jul. 12, 2001, Tan et al.

Tramontano et al., "Framework Residue 71 is a Major Determinant of the Position and Conformation of the Second Hypervariable Region in the VH Domains of Immunoglobins." *J. Mol. Biol.*, vol. 215, pp. 175-182, 1990.

U.S. Appl. No. 11/432,734, Office Action Mailed Jan. 29, 2009.
U.S. Appl. No. 11/432,734, Office Action Mailed Jun. 5, 2008.
U.S. Appl. No. 11/432,734, Office Action Mailed Sep. 4, 2007.
U.S. Appl. No. 11/432,734, Office Action Mailed Apr. 12, 2007.
U.S. Appl. No. 10/194,975, now U.S. Patent No. 6,881,557, Office Action Mailed Jul. 16, 2004.
U.S. Appl. No. 10/194,975, now U.S. Patent No. 6,881,557, Office Action Mailed Nov. 10, 2003.
U.S. Appl. No. 10/194,975, now U.S. Patent No. 6,881,557, Office Action Mailed Jul. 11, 2003.

Vajdos et al., "Comprehensive Functional Maps of the Antigen-binding Site of an Anti-ErbB2 Antibody Obtained with Shotgun Scanning Mutagenesis." *J. Mol. Biol.*, vol. 320, pp. 415-428, 2002.

Ward et al., "Binding Activities of a Repertoire of Single Immunoglobin Variable Domains Secreted from *Escherichia coli*." *Nature*, vol. 341, 544-546, Oct. 12, 1989.

Werther et al., "Humanization of an Anti-Lymphocyte Function-Associated Antigen (LFA)-1 Monoclonal Antibody and Reengineering of the Humanized Antibody for Binding to Rhesus LFA-1." *The Journal of Immunology*, vol. 157, pp. 4986-4995, 1996.

Wu et al., "Humanization of a Murine Monoclonal Antibody by Simultaneous Optimization of Framework and CDR Residues." *J. Mol. Biol.*, vol. 294, pp. 151-162, 1999.

* cited by examiner

```
           10        20         30          40         50
DIQMTQSPASLSASVGETVTITCRASGNIHNYLAWYQQKQGKSPQLLVYYTTTLAD  D1.3 Vκ   SEQ ID
                                                                      94
L23                    SqgIssY                     Yas                68
A14/DPK25              SegIgNY                     Yas                93
L1                     SqgIsNY                     aas                61
O12/DPK9               SqsIssY                     aas                54
O18/DPK1               SqdIsNY                     das                56
A30                    SqgIrNd                     aas                59
L14/DPK2               rqgIsNY                     aas                60
L4                     SqgIssa                     ass                63
L8/DPK8                SqgIssY                     aas                67
L9                     SqgIssY                     aas                69
L18                    SqgIssa                     ass                64
L15/DPK7               SqgIssw                     aas                62
L5/DPK5                SqgIssw                     ass                65
L11/DPK3               SqgIrNd                     aas                71
B2                     SqdIddd                     eaT                90
L24/DPK10              SqgIssy                     aas                70
L12                    SqsIssw                     aas                72
L6                     SqsvssY                     das                86
A26/DPK26              SqsIgss                     Yas                91
L16                    Sqsvssn                     asT                85
L2/DPK21               Sqsvssn                     gas                84

60        70         80          90         100       108
GVPSRPSGSGSGTQYSLKINSLQPEDFGSYYCQHFWSTPRTFGGGTKLEIKR       D1.3 Vκ
L23                                    yySTP
A14                                    gnkhP
L1                                     ynSyP
O12                                    sySTP
O18                                    ydnlP
A30                                    hnSyP
L14                                    hnSyP
L4                                     FnSyP
L8                                     lnSyP
L9                                     yySyP
L18                                    FnSyP
L15                                    ynSyP
L5                                     anSfP
L11                                    dynyP
B2                                     hdnfP
L24/DPK10                              yySfP
L12                                    ynSys
L6                                     rsnwP
A26                                    ssSlP
L16                                    ynnwP
L2                                     ynnwP
                                                           SEQ ID
J1                                     wTFGqGTKvEIKR       95
J2                                     yTFGqGTKLEIKR       96
J3                                     fTFGpGTKvdIKR       97
J4                                     lTFGGGTKvEIKR       98
J5                                     iTFGqGTRLEIKR       99
```

Figure 4

```
              1         2         3          4         5         6
              0         0         0          0         0         0      SEQ ID
         QVQLQESGPGLVAPSQSLSITCTVSGFSLTGYGVNWVRQPPGKGLEWLGMIWGDGNTDYNSALKS  100
         D1.3 VH

Tou-VH4.21              gSfsGYyws                      eIihsGsTnYNpsLKS   49
DP-63                   gSfsGYyws                      eInhsGsTnYNpsLKS   40
V58                     gSvsGYyws                      yIyysGsTnnNpsLKS   50
VIV-4                   gSissYyws                      rIytsGsTnYNpsLKS   51
DP-71                   gSissYyws                      yIyysGsTnYNpsLKS   42
V71-4                   gSvssYyws                      yIyysGsTnYNpsLKS   52
VH4.16                  gSissYyws                      yIyysGsTnYNpsLKS   53
DP-45                   FtfssYamh                      aIgtgGgTyYadsvKg   48
DP-48                   FtfssYdmh                      aIgtaGdTyYpgsvKg   18
DP-42                   Ftvssnyms                      vIysgGsTyYadsvKg   29
8-1B                    Ftvssnyms                      vIysgGsTyYadsvKg  101

7         8  8     8    9        10        11
              0         0  2abc  3    0         0         0
         RLSISKDNSKSQVFLKMNSLHTDDTARYYCARERDYRLDYWGQGTTLTVSS   D1.3 VH
                                                              SEQ ID
JH1                                  aeyfqhWGQGTLVTVSS       102
JH2                                  ywyfDlWGRGTLVTVSS       103
JH3                                     afDvWGQGTMVTVSS       104
JH4                                      yfDYWGQGTLVTVSS      105
JH5                                    nwfDsWGQGTLVTVSS       106
JH6                              yyydYgmDvWGQGTTVTVSS        107
```

Figure 5

```
           1         2          3         4         5                              SEQ ID
           0         0          0         0         0                              NO:
DIQMTQSPASLSASVGETVTITCRASGNIHNYLAWYQQKQGKSPQLLVYYTTTLAD  mouse D1.3 Vκ           94
AIRMTQSPFSLSASVGDRVTITCRASGNIHNYLAWYQQKPAKAPKLFIYYTTTLAD  humanized D1.3 Vκ       111

6         7          8         9         10        10
           0         0          0         0         0         8
GVPSRFSGSGSGTQYSLKINSLQPEDFGSYYCQHFWSTPRTFGGGTKLEIKR       mouse D1.3 Vκ           94
GVPSRFSGSGSGTDYTLTISSLQPEDFATYYCQHFWSTPRTFGGGTKVEIKR       humanized D1.3 Vκ      111

1         2          3         4         5         6
           0         0          0         0         0         0
QVQLQESGPGLVAPSQSLSITCTVSGFSLTGYGVNWVRQPPGKGLEWLGMIWGDGNTDYNSALKS  mouse D1.3 VH   100
QVQLQESGPGLVKPSETLSLTCTVSGGSVSGYGVNWIRQPPGKGLEWIGMIWGDGNTDYNSSLKS  humanized D1.3 VH 112

7         8 8   8    9         10        11
           0         0 2abc3    0         0         0
RLSISKDNSKSQVFLKMNSLHTDDTARYYCARERDYRLDYWGQGTTLTVSS  mouse D1.3 VH                 100
RVTISVDTSKNQFSLKLSSVTAADTAVYYCARERDYRLDYWGQGTLVTVSS  humanized D1.3 VH             112
```

SEQ ID NO: 110

```
         1200                  1220
GCCCTTGTACAACGTCAC GTAAAAAGGTATCTAGAGG TTGAGGTGATTTT
                                       >rbs 1240           1260              1280
ATG AAA AAT ATC GCA TTT CTT CTT GCA TCT ATG TTT GTT TCT TCT ATT
 M   K   N   I   A   F   L   L   A   S   M   F   V   S   S   I 380                1300            1320                 1340
GCT ACA AAC GCG TAC GCT CAG GTT CAG CTG CAG GAA TCT GGT CAG CCG GGT
 A   T   N   A   Y   A   Q   V   Q   L   Q   E   S   G   Q   P   G
|_____u_____||_____u_____
                                                        VH_u 1360                    1380                1400
CTG GTT AAG CCG TCT CAG ACT CTG ACT TGT ACT GTT TCT GGT TAC TCT GTT
 L   V   K   P   S   Q   T   L   T   C   T   V   S   G   Y   S   V
_____u_____VH_u_____

1420                     1440                  1460
ACT AGC GAC TAC GCT TGG AAC TGG ATC CGT CAG CCA CCG CCG AAA GGT CTG GAA TGG ATC GGT
 T   S   D   Y   A   W   N   W   I   R   Q   P   P   P   K   G   L   E   W   I   G
_____u_____u_____

1480              1500                 1520
TAC ATG AGC TAC TCT GGT ACT AAC TCT CTT AAA TCT CGT GTT ACT ATC TCT GTT GAC ACT TCT
 Y   M   S   Y   S   G   T   N   S   L   K   S   R   V   T   I   S   V   D   T   S
_____u_____VH_u_____

1540              1560                  1580
AAA AAC CAG TTC TCT CTG AAA CTG TCT TCT GTT ACT GCT GCT GAC ACT GCT GTT TAC TAC TGC
 K   N   Q   F   S   L   K   L   S   S   V   T   A   A   D   T   A   V   Y   Y   C
_____VH_u_____

1600                 1620               1640
GCT CGT GAA GAT TAC CGT CTG GAC TAC TGG GGC CAG GGC ACT CTG GTT ACT GTT TCT GCT TCC
 A   R   E   D   Y   R   L   D   Y   W   G   Q   G   T   L   V   T   V   S   A   S
_____u_____VH_u___

1660              1680              1700                   1720
ACT AAG GGC CCA TCG GTC TTC CCC CTG GCA CCC TCC TCC AAG AGC ACC TCT GGG GGC ACA GCG
 T   K   G   P   S   V   F   P   L   A   P   S   S   K   S   T   S   G   G   T   A
_____
 CH1_r 1740                  1760            1780              1800
GCC CTG GGC TGC CTG GTC AAG GAC TAC TTC CCC GAA CCG GTG ACG GTG TCG TGG AAC TCA GGC
 A   L   G   C   L   V   K   D   Y   F   P   E   P   V   T   V   S   W   N   S   G
_____CH1_r_____

1820                1840                1860
GCC CTG ACC AGC GGC GTG CAC ACC TTC CCG GCT GTC CTA CAG TCC TCA GGA CTC TAC TCC CTC
 A   L   T   S   G   V   H   T   F   P   A   V   L   Q   S   S   G   L   Y   S   L
_____CH1_r_____

1880             1900                1920
AGC AGC GTG GTG ACC GTG CCC TCC AGC AGC TTG GGC ACC CAG ACC TAC ATC TGC AAT GTG AAT CAC AAG CCC AGC AAC ACC AAG GTC GAC
 S   S   V   V   T   V   P   S   S   S   L   G   T   Q   T   Y   I   C   N   V   N   H   K   P   S   N   T   K   V   D
_____CH1_r_____

1940          1960              1980                  2000           2020
AAG AAA GTT GAG CCC AAA TCT TGT GAC AAA ACT CAC ACA TGC CCA CCG TGA CCGGGCATGCGACG GCCCTAGAGTCCCTAACGCT CGGTTGCCGCCGGGCGTTTT
 K   K   V   E   P   K   S   C   D   K   T   H   T   C   A   A   A   *
_____CH1_r_____                     >phage_lambda_terminator

2040
TTATTGTTAA
```

Figure 8

|  | 10 | 20 | 27abcd | 30 | 40 | 50 |  | SEQ ID NO: |
|---|---|---|---|---|---|---|---|---|
|  | DIELTQSPASLAVSLGQRATISC | RASESVEY | YVTSLMQWYQQKPGQPPKLLIF | AASNVES | 9.3 Vκ | 113 |
| B3/DPK24 |  |  | ksSqSVlYssnnknyla |  |  | wAStrES |  | 89 |
| A17 DPK18 |  |  | RsSqSlvYs dgntyln |  |  | kvSNrdS |  | 75 |
| A1/DPK19 |  |  | RsSqSlvYs dgntyln |  |  | kvSNwdS |  | 76 |
| A2/DPK12 |  |  | ksSqSllhs dgktyly |  |  | evSNrfS |  | 78 |
| A19/DPK15 |  |  | RsSqSllhs ngynyld |  |  | lgSNraS |  | 79 |
| A23/DPK16 |  |  | RsSqSlvhs dgntyls |  |  | kiSNrfS |  | 81 |
| O11/DPK13 |  |  | RsSqSlldsddgntyld |  |  | tlSyraS |  | 73 |
| A18/DPK28 |  |  | ksSqSllhs dgvtyly |  |  | evSsrfS |  | 77 |

|  | 60 | 70 | 80 | 90 | 100 | 108 |  | SEQ ID |
|---|---|---|---|---|---|---|---|---|
|  | GVPARFSGSGSGTNFSLNIHPVDEDDVAMYFC | QQSRKVPY | TFGGGTKLEIKR | 9.3 Vκ | 113 |
| B3/DPK24 |  | QQyystP |  |  |  |  |  |  |
| A17/DPK18 |  | mQgthwP |  |  |  |  |  |  |
| A1/DPK19 |  | mQgthwP |  |  |  |  |  |  |
| A2/DPK12 |  | mQSiqlP |  |  |  |  |  |  |
| A19/DPK15 |  | mQalqtP |  |  |  |  |  |  |
| A23/DPK16 |  | mQatqfP |  |  |  |  |  |  |
| O11/DPK13 |  | mQriefP |  |  |  |  |  |  |
| A18/DPK28 |  | mQgthlP |  |  |  |  |  |  |
| J1 |  |  | wTFGqGTKvEIKR |  |  |  |  | 95 |
| J2 |  |  | YTFGqGTKLEIKR |  |  |  |  | 96 |
| J3 |  |  | fTFGpGTKvdIKR |  |  |  |  | 97 |
| J4 |  |  | lTFGGGTKvEIKR |  |  |  |  | 98 |
| J5 |  |  | iTFGqGTrLEIKR |  |  |  |  | 99 |

Figure 9

```
                1         2         3         4         5         6              SEQ ID
                0         0         0         0         0         0              NO:
EVKLQQSGPGLVTPSQSLSITCTVSGFSLSDYGVHWVRQSPGQGLEWLGVIWAGGGTNYNSALMS    9.3 VH     114

DP-45                              FtfSsYamH              aIgtGGGTyYadsvKg        48
Tou-VH4.21                         gSfSgYyws              eIihsGsTNYNpsLKS        49
DP-63                              gSfSgYyws              eInhsGsTNYNpsLKS        40
VIV-4                              gSiSsYyws              rIytsGsTNYNpsLKS        51
DP-71                              gSiSsYyws              yIyysGsTNYNpsLKS        42
V71-4                              gSvSsYyws              yIyysGsTNYNpsLKS        52
VH4.16                             gSiSsYyws              yIyysGsTNYNpsLKS        53
DP-48                              FtfSsYdmH              aIgtaGdTyYpgsvKg        18
DP-42                              FtvSsnyms              VIysGGsTyYadsvKg        29
8-1B                               FtvSsnyms              VIysGGsTyYadsvKg       100
V58                                gSvSgYyws              yIyysGsTNnNpsLKS        50

7         8 8   8        9        10         11
                0         0 2abc3        0        0abcd       0
RKSISKDNSKSQVFLKMNSLQADDTAVYYCARDKGYSYYYSMDYWGQGTSVTVSS    9.3 VH    114

JH1                                         aeyfqhWGQGTlVTVSS        102
JH2                                         ywyfDlWGrGTlVTVSS        103
JH3                                            afDvWGQGTmVTVSS        104
JH4                                             yfDYWGQGTlVTVSS       105
JH5                                            nwfDsWGQGTlVTVSS        106
JH6                                         YSYdYgMDvWGQGTtVTVSS      107
```

Figure 10

```
              1         2    2        3         4         5                              SEQ ID
              0         0    7abcd 0           0         0                               NO:
DIELTQSPASLAVSLGQRATISCRASESVEYYVTSLMQWYQQKPGQPPKLLIFAASNVES   mouse 9.3 Vκ      113
DIVMTQSPDSLAVSLGERATINCRASESVEYYVTSLMAWYQQKPGQPPKLLIYAASNVES  humanized 9.3 Vκ  115

6         7         8         9        10        10
    0         0         0         0         0         8
GVPARFSGSGSGTNFSLNIHPVDEDDVAMYFCQQSRKVPYTFGGGTKLEIKR   mouse 9.3 Vκ       113
GVPDRFSGSGSGTNFSLTISSLQAEDVAVYYCQQSRKVPYTFGQGTKLEIKR   humanized 9.3 Vκ  115

1         2         3         4         5         6
         0         0         0         0         0         0
EVKLQQSGPGLVTPSQSLSITCTVSGFSLSDYGVHWVRQSPGQGLEWLGVIWAGGGTNYNSALMS   mouse 9.3 VH       114
EVQLVQSGGGLVQPGGSLRLSCAGSGFTFSDYGVHWVRQAPGKGLEWVSAIWAGGGTNYASSVMG   humanized 9.3 VH  116

7         8 8  8     9        10        11
    0         0 2abc3    0         0abcd     0
RKSISKDNSKSQVFLKMNSLQADDTAVYYCARDKGYSYYYSMDYWGQGTSVTVSS   mouse 9.3 VH      114
RFTISRDNAKNSLYLQMNSLRAEDMAVYYCARDKGYSYYYSMDYWGQGTLVTVSS   humanized 9.3 VH  116
```

Figure 12

```
            1          2    2       3          4          5                                  SEQ ID
            0          0    7abcd   0          0          0                                  NO:
DIVLTQSPVSLAVSVGQRATISCKASQSVDFDGESYMNWYQQKPGQPPKLLIYVVSNLES mouse BCF2 Vκ                    117
DIVMTQTPLSLSVTPGQPASISCKASQSVDFDGESYMNWYLQKPGQPPQLLIYVVSNLES humanized BCF2 Vκ                118

6          7    8          9          10         10
            0          0    0          0          0          8
GIPARFSGSGSGTDFTLNIHPVEEEDAATYYCQQSNEDPLTFGAGTNLELKR mouse BCF2 Vκ                           117
GVPDRFSGSGSGTDFTLKISRVEAEDVGVYYCQQSNEDPLTFGGGYKVEIKR humanized BCF2 Vκ                       118

1          2       3          4          5  5       6
            0          0       0          0          0  2a      0
EVQLQQSGPELVKPGASMKISCKVSGYSFTDHTMNWVKQSHGKNLELIGLINPFNGDATYKQKFTG mouse BCF2 VH             119
EVQLVQSGAEVKKPGATVKISCKVSGYTFTDHTMNWVQQAPGKGLEWMGLINPFNGDATYKQKFQG humanized BCF2 VH         120

7          8 8    8       9          10         11
            0          0 2abc3        0          0          0
KATLTVDRSSTAFMELLSLTSEDSAVYYCARYGNYAMDYWGQGTSVTVSS mouse BCF2 VH                             119
RVTITADTSTDTAYMELSSLRSEDTAVYYCARYGNYAMDYWGQGTTVTVSS humanized BCF2 VH                        120
```

Figure 13

```
              1         2    2        3            4              5                               SEQ ID
              0         0    7abcde   0            0              0                               NO:
**VLTQTPLSLPVSLGDQASISCRSSQSLEHNNGNTYLNWYLQKPGQSPQLLIYRVSNRFS mouse NGAD65 Vκ              121
  DVVMTQSPLSLPVTLGQPASISCRSSQSLEHNNGNTYLNWFQQRPGQSPRRLIYRVSNRFS humanized NGAD65 Vκ        122

6         7    8        9            10       10
              0         0    0        0            0        8
GGLDRFSGSGSGTDFTLKISRVEAEDLGVYFCLQVTHVPPTFGSGTKLEIKR mouse NGAD65 Vκ                       121
GVPDRFSGSGSGTDFTLKISRVEAEDVGVYYC1QVTHVPPTFGPGTKVDIKR humanized NGAD65 Vκ                   122

1         2        3            4          5 5   5       6
              0         0        0            0          0·2a  6       0
QVQLQQPGAELVKPGASVKMSCKASGYRFSSYNMHWVKQTPGQGLEWIGAIYPRSGDTSYN mouse NGAD65 VH              123
EVQLLQSAAEVKRPGESLRISCKTSGYSFTSYNMHWVRQMPGKELEWMGAIYPRSGDTSYN humanized NGAD65 VH          124

7         8 8    8        9     9      10            11
              0         0 2abc3         0     4      0ab           0
QKFKGRATLTADKSSSTAYMQLGSLTSEDSAVYYCVRSYDYDAPFAFWGQGTLVTVSA mouse NGAD65 VH                 123
PSFQGHVTISADSSSSTAYLQWSSLKASDAAMYYCVRSYDYDAPFAFWGQGTLVTVSS humanized NGAD65 VH             124
```

SUPER HUMANIZED ANTIBODIES

CROSS-REFERENCE TO RELATED APPLICATION

The present application is a divisional of Ser. No. 10/194,975, filed Jul. 12, 2002, now U.S. Pat. No. 6,881,557, which is a nonprovisional and claims the benefit of provisional application 60/305,111 filed Jul. 12, 2001.

STATEMENT OF GOVERNMENT INTEREST

Development of this invention was supported, in part, by a grant from the U.S., National Institute of Health, grant number CVA-18029.

TECHNICAL FIELD

The invention relates to methods of humanizing antibodies, particularly to humanizing antibodies by making chimeric antibodies containing CDR sequences from a non-human antibody and framework sequences of human antibodies, more particularly to methods of selecting appropriate human antibody framework sequences for performing the humanization, and still more particularly to using canonical CDR structure types of the non-human antibody in comparison to germline canonical CDR structure types of human antibodies as the basis for selecting the appropriate human framework sequences for a humanized antibody.

BACKGROUND OF THE INVENTION

Antibodies are natural proteins that the vertebrate immune system forms in response to foreign substances (antigens), primarily for defense against infection. For over a century, antibodies have been induced in animals under artificial conditions and harvested for use in therapy or diagnosis of disease conditions, or for biological research. Each individual antibody producing cell produces a single type of antibody with a chemically defined composition, however, antibodies obtained directly from animal serum in response to antigen inoculation actually comprise an ensemble of non-identical molecules (i.e, polyclonal antibodies) made from an ensemble of individual antibody producing cells.

Hybridoma technology provided a method to propagate a single antibody-producing cell for an indefinite number of generations with a screening method to identify clones of cells producing an antibody that would react with a particular antigen. Development of this technology allowed production in unlimited quantities of structurally identical antibodies with essentially any desired antigenic specificity. Such antibodies are commonly called monoclonal antibodies, and most originate from rodents. Sequencing of monoclonal antibody genes allowed the primary amino acid structure of the antibody be defined.

The advent of recombinant DNA methodology enabled structural engineering of antibody genes and production of modified antibody molecules with properties not obtainable by hybridoma technology. In the therapeutic arena, one aim of this methodology has been to reduce the immunogenicity in humans of rodent monoclonal antibodies by modifying their primary amino acid structure. Reduction of the immunogenicity of therapeutic antibodies is desirable because induction of an immune response can cause a spectrum of adverse effects in a patient, ranging from accelerated elimination of the therapeutic antibody, with consequent loss of efficacy, to fatal anaphylaxis at the most extreme.

One strategy to reduce immunogenicity of foreign monoclonal antibodies has been to replace the light and heavy chain constant domains of the monoclonal antibody with analogous domains of human origin leaving the variable region domains of the foreign antibody intact. The variable region domains of the light and heavy chains are responsible for the interaction between the antibody and the antigen. The joining domains connecting variable domains to constant domains are situated in a region remote from the site of antigen binding, therefore, the joining domains between variable and constant domains generally do not interfere with antigen binding. Chimeric antibody molecules having mouse variable domains joined to human constant domains usually bind antigen with the same affinity constant as the mouse antibody from which the chimeric was derived. Such chimeric antibodies are less immunogenic in humans than their fully murine counterparts. Nevertheless, antibodies that preserve entire murine variable domains tend to provoke immune responses in a substantial fraction of patients. For example, INFLIXMAB™, a widely prescribed chimeric antibody that is considered safe, induced a human anti-chimeric antibody response in 7 out of 47 Crohns Disease patients. (Rutgeerts, P., et al (1999) *Efficacy and safety of retreatment with anti-tumor necrosis factor antibody (INFLIXIMAB) to maintain remission in Crohn's disease*. Gastroenterology 117, 761-769).

That humans would mount an immune response to whole murine variable domains was predictable, thus, efforts to obtain variable domains with more human character had begun even before clinical trials of such standard chimeric antibodies had been reported. One category of methods frequently referred to as "humanizing," aims to convert the variable domains of murine monoclonal antibodies to a more human form by recombinantly constructing an antibody variable domain having both mouse and human character. Humanizing strategies are based on several consensual understandings of antibody structure data. First, variable domains contain contiguous tracts of peptide sequence that are conserved within a species, but which differ between evolutionarily remote species, such as mice and humans. Second, other contiguous tracts are not conserved within a species, but even differ even between antibody producing cells within the same individual. Third, contacts between antibody and antigen occur principally through the non-conserved regions of the variable domain. Fourth, the molecular architecture of antibody variable domains is sufficiently similar across species that correspondent amino acid residue positions between species may be identified based on position alone, without experimental data.

Humanized strategies share the premise that replacement of amino acid residues that are characteristic of murine sequences with residues found in the correspondent positions of human antibodies will reduce the immunogenicity in humans of the resulting antibody. However, replacement of sequences between species usually results in reduction of antibody binding to its antigen. The art of humanization therefore lies in balancing replacement of the original murine sequence to reduce immunogenicity with the need for the humanized molecule to retain sufficient antigen binding to be therapeutically useful. This balance has been struck using two approaches.

In one approach, exemplified by U.S. Pat. No. 5,869,619 to Studnicka and by Padlan (1991) *A possible procedure for reducing the immunogenicity of antibody variable domains while preserving their ligand binding properties*, Molecular Immunology 28:489-498, characteristically human residues are substituted for murine variable domain residues that are determined or predicted (i) to play no significant chemical role in the interaction with antigen, and (ii) to be positioned with side chains projecting into the solvent, Thus, exterior residues remote from the antigen binding site are humanized, while interior residues, antigen binding residues, and residues forming the interface between variable domains remain murine. One disadvantage of his approach is that rather extensive experimental data is required to determine whether a residue plays no significant chemical role in antigen binding or will be positioned in the solvent in a particular three dimensional antibody structure.

In another more general approach, exemplified by U.S. Pat. No. 5,225,539 to Winter and by Jones et al (1986) *Replacing the complementarity determining regions in a human antibody with those from a mouse*, Nature 321:522-525, contiguous tracts of murine variable domain peptide sequence considered conserved are replaced with the correspondent tracts from a human antibody. In this more general approach, all variable domain residues are humanized except for the non-conserved regions implicated in antigen binding. To determine appropriate contiguous tracks for replacement, Winter, and Jones et al (1986) utilized a classification of antibody variable domain sequences that had been developed previously by Wu and Kabat (1970).

Wu and Kabat pioneered the alignment of antibody peptide sequences, and their contributions in this regard were several-fold: First, through study of sequence similarities between variable domains, they identified correspondent residues that to a greater or lesser extent were homologous across all antibodies in all vertebrate species, inasmuch as they adopted similar three-dimensional structure, played similar functional roles, interacted similarly with neighboring residues, and existed in similar chemical environments. Second, they devised a peptide sequence numbering system in which homologous immunoglobulin residues were assigned the same position number. One skilled in the art can unambiguously assign what is now commonly called Kabat numbering, to any variable domain sequence, without reliance on any experimental data beyond the sequence itself. Third, for each Kabat-numbered sequence position, Kabat and Wu calculated variability, by which is meant the finding of few or many possible amino acids when variable domain sequences are aligned. They identified three contiguous regions of high variability embedded within four less variable contiguous regions. Other workers had previously noted variability approximately in these regions (hypervariable regions) and posited that the highly variable regions represented amino acid residues used for antigen binding. Kabat and Wu formally demarcated residues constituting these variable tracts, and designated these "complementarity determining regions" (CDRs), referring to chemical complementarity between antibody and antigen. A role in three-dimensional folding of the variable domain, but not in antigen recognition, was ascribed to the remaining less-variable regions, which are now termed "framework regions". Fourth, Kabat and Wu established a public database of antibody peptide and nucleic acid sequences, which continues to be maintained and is well known to those skilled in the art.

The humanization method disclosed by Winter and Jones using the Kabat classification results in a chimeric antibody comprising CDRs from one antibody and framework regions from another antibody that differs in species origin, specificity, subclass, or other characteristics. However, no particular sequences or properties were ascribed to the framework regions, indeed, Winter taught that any set of frameworks could be combined with any set of CDRs. Framework sequences have since been recognized as being important for conferring the three dimensional structure of an antibody variable region necessary retain good antigen binding. Thus, the general humanizing methods described by Winter and Jones have the disadvantage of frequently leading to inactive antibodies because these references do not provide information needed to rationally select among the many possible human framework sequences, those most likely to support antigen binding required by a particular CDR region from a non-human antibody. Subsequent developments in the field have been refinements within the scope of Winter to deal with loss of avidity for antigen observed with some humanized antibodies relative to the avidity of the corresponding mouse antibodies. (Avidity is a quantitative measure of partitioning of an antibody, in the presence of antigen under conditions approximating chemical equilibrium, between free and antigen-bound forms. For reactions in solution not subject to multivalent binding effects, avidity is the same as affinity, the biochemical equilibrium constant.).

U.S. Pat. No. 5,693,761 to Queen et al, discloses one refinement on Winter for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, Queen teaches using human framework sequences closely homologous in linear peptide sequence to framework sequences of the mouse antibody to be humanized. Accordingly, the methods of Queen focus on comparing framework sequences between species. Typically, all available human variable domain sequences are compared to a particular mouse sequence and the percentage identity between correspondent framework residues is calculated. The human variable domain with the highest percentage is selected to provide the framework sequences for the humanizing project. Queen also teaches that it is important to retain in the humanized framework, certain amino acid residues from the mouse framework critical for supporting the CDRs in a binding-capable conformation. Potential criticality is assessed from molecular models. Candidate residues for retention are typically those adjacent in linear sequence to a CDR or physically within 6 Å of any CDR residue.

In other approaches, criticality of particular framework amino acid residues is determined experimentally once a low-avidity humanized construct is obtained, by reversion of single residues to the mouse sequence and assaying antigen binding as described by Riechmann et al, (1988). Another example approach for identifying criticality of amino acids in framework sequences is disclosed by U.S. Pat. No. 5,821,337 to Carter et al, and by U.S. Pat. No. 5,859,205 to Adair et al. These references disclose specific Kabat residue positions in the framework, which, in a humanized antibody may require substitution with the correspondent mouse amino acid to preserve avidity. One of the disadvantages of the refinements by Queen, and the approaches of Ricechmann, Carter and Adair, is that a very large number of human framework sequences are required for comparison, and/or the guidelines for preserving critical amino acid residues are not completely sufficient to predict functionality. Accordingly, the resulting frameworks constructed, which are part human and part mouse, still frequently exhibit human immunogenicity or lowered antigen binding, thereby requiring numerous iterations in framework construction to obtain a suitable framework for therapeutic uses.

A second type of refinement to Winter is exemplified by Padlan et al (1995) *Identification of specificity-determining residues in antibodies*, FASEB J. 9:133-139; and Tamura et al (2000) *Structural correlates of an anti-carcinoma antibody:*

*identification of specificity-determining residues (SDRs) and development of a minimally immunogenic antibody variant by retention of SDRs only.* J. Immunol. 164:1432-1441. These references share the premise that increasing the proportion of characteristically human sequence in a humanized antibody will reduce that antibody's immunogenicity, and accordingly disclose methods for grafting partial CDR sequences. Determination of the three-dimensional structure of antibody-antigen complexes showed that many residue positions assigned to the CDRs defined by Kabat and Wu rarely were directly involved in antigen binding. These references showed that grafting a subset of CDR residues would adequately transfer antigen binding in a humanized antibody. However, humanized framework sequences are still required, and these references do not teach methods for selecting adequate human framework sequences for use with a given set of mouse CDRs.

There is therefore, a need in the art for methods of humanizing antibodies that reliably identify suitable human framework sequences to support non-human CDR regions and to provide humanized antibodies that retain high antigen binding with low immunogenicity in humans, without the need for direct comparison of framework sequences, without need for determining critically important amino acid residues in the framework, and without need for multiple iteration constructions to obtain humanized antibodies with suitable therapeutic properties.

SUMMARY OF THE INVENTION

The present invention meets this need by providing methods for making humanized antibody of high affinity and low immunogenicity without need for comparing framework sequences between non-human and human antibodies and also provides humanized antibodies made thereby. Rather than relying on human framework sequences as the point of analysis, the methods provided herein rely on comparing canonical CDR structure types of the non-human antibody to CDR structure types of human antibodies, particularly as encoded by human germline sequences, to identify candidate human antibody sequences from which to obtain appropriate human frameworks.

More particularly, there is provided a method of making a humanized antibody that includes the acts of obtaining a peptide sequence for a subject variable region encoded by a non-human mature antibody gene and identifying a first set of canonical CDR structure types for at least two CDRs within the non-human antibody variable region. Then A library of peptide sequences for human antibody variable regions for human antibodies is also obtained. In a preferred embodiment, the library contains sequences for human germline variable regions as encoded by germline nucleic acid segments. In other embodiments, however, the library may include mature human antibody sequences. In either case, the method includes identifying canonical CDR structure types (i.e., a second set of canonical CDR structure types) for at least two CDRs for each sequence within the library of human variable region sequences. From this library there is selected a subset of candidate sequences by comparing the first set of canonical CDR structure types to the second set of canonical CDR structure types (i.e., comparing the mouse canonical CDR structure types to the human canonical CDR structure types at corresponding locations within the variable region) and selecting those human sequences where the second set of canonical CDR structure is the same as the first set of canonical CDR structure types for the CDR sequences at corresponding locations within the non-human and human variable regions, respectively. The method uses these candidate human variable region sequences as a basis for constructing a chimeric molecule that includes at least two of the CDR sequences from the non-human variable region (e.g., of the mouse CDRs) combined with the framework regions from candidate human variable region sequences. The result of the construction is that the chimeric antibody contains each of the non-human CDR sequences substituted for each of the human CDR sequences at corresponding locations in the variable regions so that the framework sequences in the chimeric antibody differs from the candidate human framework sequences by no more than 10 amino acid residues. In certain embodiments, the framework sequences of the chimeric antibody differ from the human framework sequences by no more than 5 amino acid residues. In other embodiments, the framework sequences of the chimeric antibody differs from the human framework sequences by no more than 2 amino acid residues. In most embodiments, the act of constructing the chimeric antibody molecule includes constructing a nucleic acid sequence that encodes the chimeric antibody sequences.

In typical embodiments, the method further includes ranking the members of the subset of candidate human sequences by comparing position by position similarity of amino acid residues of the non-human CDR sequences to the corresponding human CDR sequences according to a ranking criterion. In certain practices, the candidate of human sequences includes only the top 25% of the ranked members. In some embodiments, the ranking criterion includes a score of amino acid identity between the non-human and human CDR sequences at corresponding residue positions of at least one CDR, or at least two CDRs, or most typically each corresponding CDR. In other embodiments, the ranking criterion includes a score of amino acid homology between the non-human and human CDRs at corresponding residue positions of at least one, at least two, or each of the corresponding CDRs. In still other embodiments, the ranking criterion includes both a score of amino acid identity as well as a score of amino acid homology for at least one, at least two or each of the corresponding CDRs. The method may be practiced using CDRs as defined by differing systems. For example, in certain embodiments, the CDRs are Kabat defined CDRs, in other embodiments, the CDRs are Chothia defined CDR loops.

The method is not limited to strictly using the exact CDR sequences of the non-human source or exact sequences of the human frameworks from the member sets. In certain embodiments, the method may also include substituting at least one amino acid residue of the non-human CDR sequences with a different amino acid, provided however, that no more than 4 residues are substituted in any of non-human light chain CDR1, light chain CDR2, light chain CDR3, heavy chain CDR1, or heavy chain CDR3 and no more than 10 amino acids are substituted in non-human heavy chain CDR2. In other embodiments, the method may also include substituting at least one but no more than 10 amino acid residues of the human framework sequence with a different amino acid residue.

The method also recognizes that on certain occasions the non-human variable region may include a CDR sequence having a canonical type absent from human variable regions. In cases where each of three non-human CDRs is a light chain CDR, if one of three non-human CDR sequences is of a canonical structure type absent from the library of human variable region sequences, then the act of selecting the human sequences includes selecting a human variable region sequence with a CDR of a different canonical type than the absent non-human CDR type at the corresponding location, providing only that the different canonical human CDR type has a length no more than two amino acid residues smaller or larger than the length of the absent canonical CDR structure type of the non-human CDR. Typically, if the absent CDR sequences is of canonical type 1, then the act includes selecting a human sequence with a canonical type 2 CDR at the corresponding location, or if the non-human CDR sequences is of canonical type 5 then the act includes selecting a human sequence with a canonical type 4 or 3 CDR at the corresponding location.

In most embodiments, the non-human variable region is a mouse variable region. Similarly, in most embodiments the library of human variable region sequences includes a human $V_k$, $V_\lambda$, $V_H$, $J_H$, $J_k$ or $J_\lambda$ sequence as the source of the human frameworks. In most embodiments, the method includes assembling a chimeric antibody having both a chimeric variable light chain and a chimeric variable heavy chain, typically with human frameworks from $V_k$ and $V_H$ sequences. In typical embodiments, the chimeric variable light chains and chimeric variable heavy chains are formed into an Fab fragment, or a (Fab)'$_2$ molecule, or a single chain Fv molecule, or the chimeric variable light chains and chimeric heavy chains are assembled with a human antibody constant region to form a complete antibody.

The methods are applicable to converting a subject antibody sequence of any subject species to a less immunogenic form suitable for use in an object species by making chimeric antibodies containing framework sequences of the object species in combination with CDRs from the subject species. In such cases, the foregoing methods are the same in the acts performed, where the variable region may be from any subject species and the object variable region may be from any object species for which the antibody will be used. Thus, for example, in various embodiments, a subject antibody may be chimierzied with framework sequences from bovine, porcine, murine or equine sources to form bovinized, porcinized, murinized, or equinized, respectively.

In another aspect, the invention provides compositions that include the chimeric antibody molecules made according to the disclosed methods. Because, the methods utilize a novel way of identifying the appropriate object framework sequence to combine with subject CDR sequences, the resulting chimeric antibodies made are also novel. Accordingly, there is herein provided, a humanized antibody that includes a chimeric antibody variable region containing at least two non-human CDR sequences fused adjacent to human variable region framework sequence. The human framework sequences are selected from a subset of framework sequences characterized by having no more than 10 amino acid residues that differ from a framework sequences in a human antibody variable region having at least two human CDR sequences with the same canonical structure type as the non-human CDR sequences for at least two corresponding CDR positions between the variable region of the chimeric antibody and the human antibody.

The non-human variable region CDRs are typically from a mouse. The human variable region sequence is typically a $V_k$, $V_\lambda$, $V_H$, $J_H$, $J_k$ or $J_\lambda$ sequence. Most typically the chimeric antibody includes chimeric antibody sequences for each of a variable light chain and a variable heavy chain. In typical embodiments, the chimeric variable light chains and chimeric variable heavy chains are formed into an Fab fragment, or a (Fab)'$_2$ molecule, or a single chain Fv molecule, or the chimeric variable light chains and chimeric heavy chains are assembled with a human antibody constant region in the form of a complete antibody. Most typically, the human variable region sequence is a sequence from a human germline variable region fragment. In other embodiments, the human variable regions sequence is a sequence from a human mature antibody.

In preferred embodiments, the humanized antibody has a dissociation constant for its antigen of at least $10^6$ M$^{-1}$, preferably at least $10^7$ M$^{-1}$ and more preferably at least $10^8$ M$^{-1}$. Typically the humanized antibody of does not elicit an immune response when administered to a human. Particular embodiments exemplifying the invention included humanized antibodies that bind a scorpion venom antigen, that bind a human CD28 receptor, that bind human lysozyme, or that bind a human glutamic acid decarboxylase (GAD65).

BRIEF DESCRIPTION OF THE DRAWINGS

FIG. 1 depicts a library of human germline $V_H$ gene segments (SEQ ID NOS:1-53).

FIG. 2 depicts a library of human germline $V_k$ gene segments (SEQ ID NOS:54-93).

FIG. 3 depicts a portion of mouse D1.3 (anti-chicken lysozyme) antibody variable light chain sequence (SEQ ID NO:94) and a selected subset of human germline $V_k$ variable region sequences (SEQ ID NOS:54, 56, 59-65, 67-72, 84-86, 90, 91, 93, 95-99) having canonical CDRs of the same type as the mouse DL.3 light chain sequence at corresponding locations. The subset is ranked by similarity of amino acid sequences between the DL.3 CDRs and the human CDRs, with the highest ranked sequence depicted first.

FIG. 4 depicts a portion of the mouse D1.3 antibody variable heavy chain sequence (SEQ ID NO:100) and a selected subset of human germline VH variable region sequences (SEQ ID NOS:18, 29, 40, 42, 48-53, 101-107) having canonical CDRs of the same type as the DL.3. The subset is ranked by similarity of amino acid sequences of the corresponding CDRs analoaously to FIG. 3.

FIG. 5 depicts amino acid sequences for a chimeric $V_k$ variable region (SEQ ID NOS:94 and 111) and $V_H$ variable region for a humanized D1.3 antibody (SEQ ID NOS:100 and 112), illustrating one aspect of the invention.

FIGS. 6 and 6A depict a nucleic acid sequence for a DNA construct (SEQ ID NO:108) that encodes (and expresses) the humanized chimeric D1.3 antibody (SEQ ID NOS:109 and 110) of FIG. 5, illustrating another aspect of the invention.

FIG. 8 depicts a portion of a mouse variable light chain sequence of an anti-human CD28 antibody designated 9.3 (SEQ ID NO:113) and a selected subset of human germline $V_k$ variable region sequences (SEQ ID NOS:73, 75-79, 81, 89, 95-99) having canonical CDRs of the same type as the mouse 9.3 variable light chain sequence at corresponding locations, which are ranked by similarity of amino acid seciuences analagously to FIG. 3.

FIG. 9 depicts a portion of the mouse variable heavy chain sequence for the 9.3 antibody (SEQ ID NO:114) and a selected subset of human germline $V_H$ variable region sequences (SEQ ID NOS:18, 29, 40, 42, 48-53, 100, 102-107) having canonical CDRs of the same type as the mouse variable heavy chain sequence at corresponding locations also ranked by similarity of amino acid sequences.

FIG. 10 depicts a humanized anti-human CD28 (Hu.9.3) Fab fragment with chimeric variable heavy (SEQ ID NOS: 114 and 116) and variable light chains (SEQ ID NOS:113 and 115), illustrating another embodiment of the invention.

FIG. 12 depicts a humanized anti-scorpion toxin Fab fragment with chimeric variable heavy (SEQ ID NOS:119 and 120) and variable light chains (SEQ ID NOS:117 and 118) illustrating another embodiment of the invention.

FIG. 13 depicts a humanized anti-human glutamic acid decarboxylase (GAD65) Fab fragment with chimeric variable heavy (SEQ ID NOS:123 and 124) and variable light chains, (SEQ ID NOS:121 and 122), illustrating another embodiment of the invention.

DETAILED DESCRIPTION OF THE INVENTION

Figure 7:
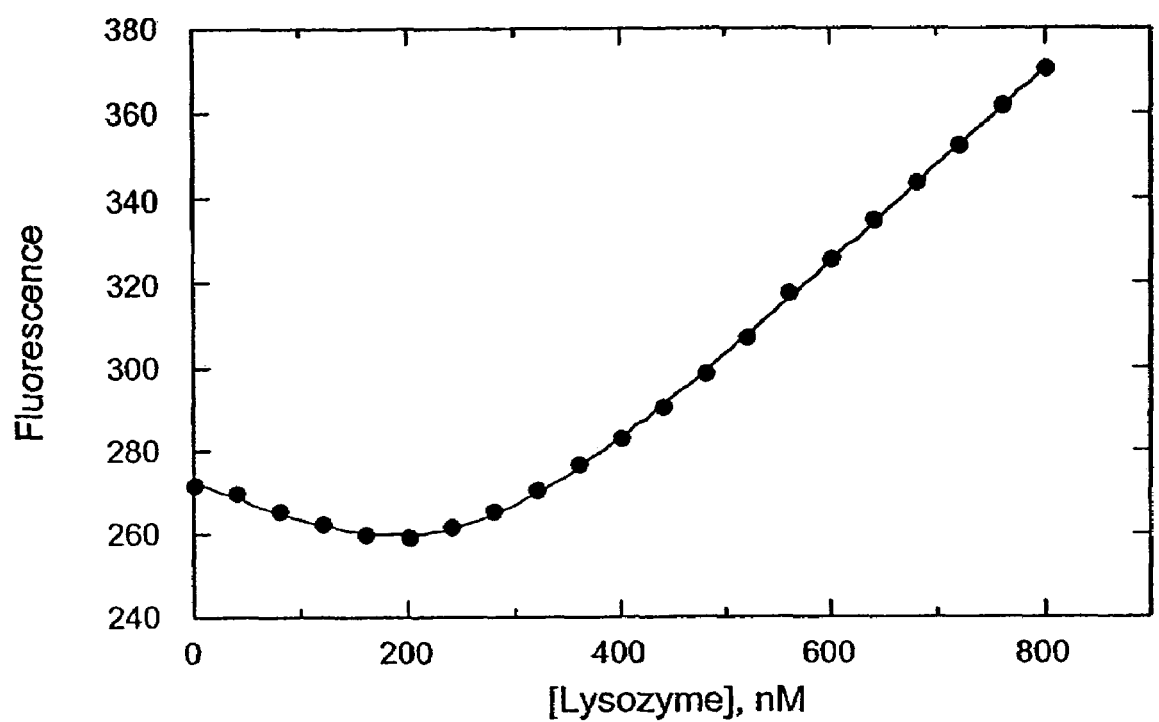
FIG. 7 is a graph that illustrates antigen binding by the humanized D1.3 antibody, which has an affinity constant of greater than $10^8$ M$^{-1}$, illustrating one embodiment of the invention.

In the description that follows, citation is made to various references that may assist one of ordinary skill in the art in understanding the invention and practicing the invention to its fullest extent. Therefore, each reference cited in the description that follows is incorporated herein by reference in its entirety. To better aid in understanding various embodiments of the invention it may be helpful to explain the meanings of certain terms used herein.

A "mature antibody gene" is a genetic sequence encoding an immunoglobulin that is expressed, for example, in a lymphocyte such as a B cell, in a hybridoma or in any antibody producing cell that has undergone a maturation process so that the particular immunoglobulin is expressed. The term includes mature genomic, cDNA or other nucleic acid sequence that encodes such mature genes, which have been isolated and/or recombinantly engineered for expression in other cell types. Mature antibody genes have undergone various mutations and rearrangements that structurally distinguish them from antibody genes encoded in all cells other than lymphocytes. Mature antibody genes in humans, rodents, and many other mammals are formed by fusion of V and J gene segments in the case of antibody light chains and fusion of V, D, and J gene segments in the case of antibody heavy chains. Many mature antibody genes acquire point mutations subsequent to fusion, some of which increase the affinity of the antibody protein for a specific antigen.

Figure 1:
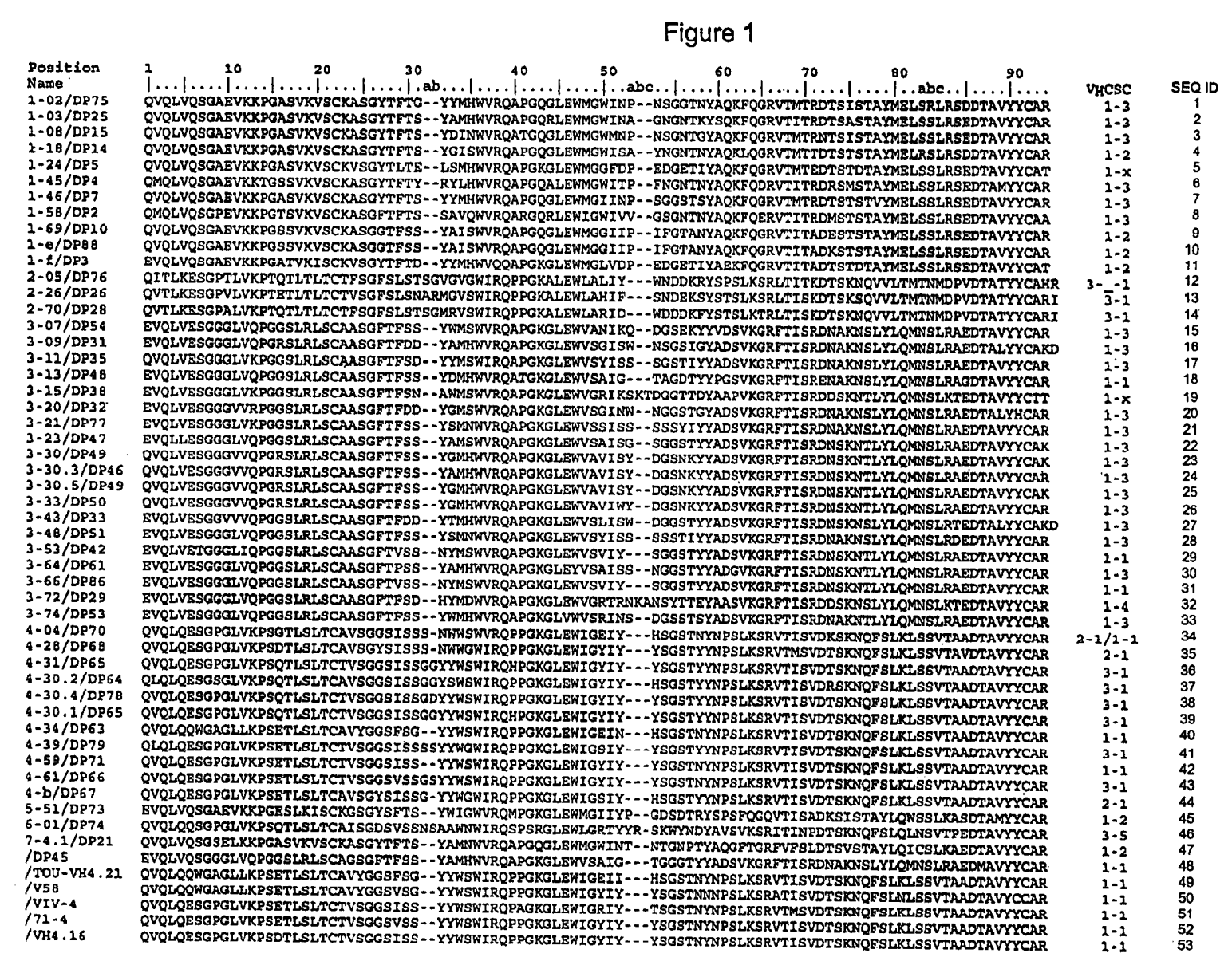

"Germline antibody genes" or gene fragments are immunoglobulin sequences encoded by non-lymphoid cells that have not undergone the maturation process that leads to genetic rearrangement and mutation for expression of a particular immunoglobulin. One of the advantages provided by various embodiments of the present invention stems from the recognition that germline antibody genes are more likely than mature antibody genes to conserve essential amino acid sequence structures characteristic of individuals in the animal species, hence less likely to be recognized as from a foreign source when used therapeutically in that species. FIG. 1 (SEQ ID NOS:1-53) and FIG. 2 (SEQ ID NOS:54-93) show peptide sequences for human germline antibody genes encoding human variable heavy region ($V_H$) and variable light region ($V_k$) antibodies (i.e., immunoglobulins). Each of these list of sequences exemplify a library of human antibody genes, particularly a library of human germline antibody genes.

"A CDR" is the complement determining region within antibody variable sequences. There are three CDRs in each of the variable heavy and variable light sequences designated CDR1, CDR2 and CDR3, for each of the variable regions. The exact boundaries of these CDRs have been defined differently according to different systems, however, all have overlapping residues in what constitute the so called "hypervariable regions" within the variable sequences. The system described by Kabat (CITE) not only provides an unambiguous residue numbering system applicable to any variable region of an antibody, but also provides precise residue boundaries defining the three CDRs. These CDRs may be referred to as Kabat CDRs. Chothia and coworkers (CITE) found that certain sub portions within Kabat CDRs adopt nearly identical peptide backbone conformations, despite having great diversity at the level of amino acid sequence. These sub portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Table I illustrates the overlap Chothia and Kabat CDRs according to the residue numbering system of Kabat.

TABLE I

| Chain | CDR | Kabat | Chothia |
|---|---|---|---|
| Light | CDR1 | 24-34 | 26-32 |
| " | CDR2 | 50-56 | 50-52 |
| " | CDR3 | 89-96 | 91-96 |
| Heavy | CDR1 | 31-35 | 26-32 |
| " | CDR2 | 50-65 | 52-56 |
| " | CDR3 | 95-102 | not uniquely defined |

Other boundaries defining CDRs overlapping with the Kabat CDRs have been described by Padlan (1995) or MacCallum (1996). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Clothia defined CDRs.

"Framework" or "framework sequence" are the remaining sequences of a variable region minus the CDRs. Because the exact definition of a CDR sequence can be determined by different systems, the meaning of a framework sequences is subject to correspondingly different interpretations. To clarify the meaning used herein, a framework sequence means those sequences within the variable region of an antibody other than those defined to be CDR sequences, so that the exact sequence of a framework depends only on how the CDR is defined. For example, the CDRs used in the methods provided herein are usually a subset of what is considered a Kabat CDR, but in the case of CDR1 of heavy chains for example, also includes residues that are classified as framework residues in the Kabat system.

"Canonical CDR structure types" are the structure types designated by Chothia (CITE). Chothia and coworkers found that critical portions of the CDRs of many antibodies adopt nearly identical peptide backbone conformations, despite great diversity at the level of amino acid sequence. Accordingly, Chothia defined for each CDR in each chain one or a few "canonical structures". Each canonical structure specifies primarily a set of peptide backbone torsion angles for a contiguous segment of amino acid residues forming a loop. The canonical CDR structure types defined by Chothia are listed in Table II.

TABLE II

| Chain | CDR | Canonical structure types |
|---|---|---|
| Kappa | CDR1 | 1-6 |
| " | CDR2 | 1 |
| " | CDR3 | 1-6 |
| Heavy | CDR1 | 1-3 |
| " | CDR2 | 1-4 |
| Lambda | CDR1 | 1-4 |
| " | CDR2 | 1 |
| " | CDR3 | 1-2 |

"Corresponding CDRs" refer relatively to the CDRs between two different variable sequences that correspond in position within the two different variable sequences. Thus, for example, a mouse light chain CDR1 corresponds to a human light chain CDR1, and vice a versa, because each maps to a defined position in a Kabat numbering system, whether or not the actual boundary of the CDR is defined by Kabat, Chothia or some other system. Similarly, "corresponding" residues, sequences or amino acids refer relatively to the residue positions between two different peptide sequences mapped by the Kabat numbering system.

The objective of the methods provided herein, which may be called CDR grafting, method is to provide a prescription for arriving at appropriate human framework sequence for humanizing a subject non-human antibody. In all previous CDR grafting methods, the choice of the humanized framework sequence was based on comparing the human framework to the subject (murine) frameworks. In contrast, the basis of the methods herein described are to chose the human antibody to provide the humanized framework based on similarity of its CDRs to those of the subject antibody, without regard to comparing the framework sequences between the two antibodies.

The similarity to the subject CDRs of candidate human antibody sequences is assessed for each domain at two levels. Primarily, identical three-dimensional conformations of CDR peptide backbones are sought. Experimentally determined atomic coordinates of the subject CDRs are seldom available, hence three-dimensional similarity is approximated by determining Chothia canonical structure types of the subject CDRs and excluding from further consideration candidates possessing different canonical structures. Secondarily, residue-to-residue homology between subject CDRs and the remaining human candidate CDRs is considered, and the candidate with the highest homology is chosen.

Choosing highest homology is based on various criterion used to rank candidate human variable regions having the same canonical structure as the subject the non-human variable regions. The criterion for ranking members of the selected set may be by amino acid sequence identity or amino acid homology or both. Amino acid identity is simple a score of position by position matches of amino acid residues. Similarity by amino acid homology is position by position similarity in residue structure of character. Homology may be scored, for example, according to the tables and procedures described by Henikoff and Henikoff, (1992) *Amino acid substitution matrices from protein blocks*, Proc. Natl. Acad. Sci 89: 10915-10919; or by the BLOSUM series described by Henikoff and Henikoff, (1996).

The steps of the methods are as follow:

Determine the peptide sequences of the heavy and light chain variable domains of the subject antibody. These can be determined by any of several methods, such as DNA sequencing of the respective genes after conventional cDNA cloning; DNA sequencing of cloning products that have been amplified by the polymerase chain reaction from reverse transcripts or DNA of the subject hybridoma line; or peptide sequencing of a purified antibody protein.

Apply the Kabat numbering system (Kabat et al, 1991) to the heavy and light chain sequences of the subject non-human antibody.

Determine canonical structure types for each of the CDRs of the subject non-human antibody. This determination is made from examination of the peptide sequence in light of the guidelines discussed in Chothia and Lesk (1987), Chothia et al (1992), Tomlinson et al (1995), Martin and Thornton (1996), and Al-Lazikani et al (1997). The salient features of canonical structure determination for each of the CDRs are as follows.

For heavy chain CDR1, three canonical structure types are currently known. Assignment of a new sequence is straightforward because each canonical structure type has a different number of residues. As described in Al-Lazikani et. al (1997), when Kabat numbering is assigned to the sequence, the numbering for residues 31-35 will be as follows for the respective canonical structures.

Canonical structure type 1: 31, 32, 33, 34, 35.
Canonical structure type 2: 31, 32, 33, 34, 35, 35a.
Canonical structure type 3: 31, 32, 33, 34, 35, 35a, 35b.

For heavy chain CDR2, four canonical structure types are currently known. Several have unique numbers of residues, and are easily distinguished from their unique Kabat numbering of positions 52-56, viz.:

Canonical structure type 1: 52, 53, 54, 55, 56.
Canonical structure type 4: 52, 52a, 52b, 52c, 53, 54, 55, 56.

Canonical structure types 2 and 3 for heavy chain CDR2 have equal numbers of residues, hence must be distinguished by clues within their sequence, as discussed by Chothia et al (1992). The Kabat numbering of the segment containing these clues is: 52, 52a, 53, 54, 55. Canonical structure type 2 has Pro or Ser at position 52a and Gly or Ser at position 55, with no restriction at the other positions. Canonical structure type 3 has Gly, Ser, Asn, or Asp at position 54, with no restriction at the other positions. These criteria are sufficient to resolve the correct assignment in most cases. Additionally framework residue 71 is commonly Ala, Val, Leu, Ile, or Thr for canonical structure type 2 and commonly Arg for canonical structure type 3.

Heavy chain CDR3 is the most diverse of all the CDRs. It is generated by genetic processes, some of a random nature, unique to lymphocytes. Consequently, canonical structures for CDR3 have been difficult to predict. In any case, human germline V gene segments do not encode any part of CDR3; because the V gene segments end at Kabat position 94, whereas positions 95 to 102 encode CDR3. For these reasons, canonical structures of CDR3 are not considered for choosing candidate human sequences.

For light chain CDR1, six canonical structure types are currently known for CDR1 in kappa chains. Each canonical structure type has a different number of residues, hence assignment of a canonical structure type to a new sequence is apparent from the Kabat numbering of residue positions 27-31.

Canonical structure type 1: 27, 29, 30, 31.
Canonical structure type 2: 27, 28, 29, 30, 31.
Canonical structure type 3: 27, 27a, 27b, 27c, 27d, 27e, 27f, 28, 29, 30, 31.
Canonical structure type 4: 27, 27a, 27b, 27c, 27d, 27e, 28, 29, 30, 31.

Canonical structure type 5: 27, 27a, 27b, 27c, 27d, 28, 29, 30, 31.

Canonical structure type 6: 27, 27a, 28, 29, 30, 31.

For light chain CDR2, only a single canonical structure type is known for CDR2 in kappa chains, hence, barring exceptional subject antibody sequences, assignment is automatic.

For light chain CDR3, up to six canonical structure types have been described for CDR3 in kappa chains, but three of these are rare. The three common ones can be distinguished by their length, reflected in Kabat numbering of residue positions 91-97:

Canonical structure type 1: 91, 92, 93, 94, 95, 96, 97 (also with an obligatory Pro at position 95 and Gln, Asn, or His at position 90).

Canonical structure type 3: 91, 92, 93, 94, 95, 97.

Canonical structure type 5: 91, 92, 93, 94, 95, 96, 96a, 97.

After identifying the canonical CDR structure types of the subject non-human antibody, human genes of the same chain type (heavy or light) that have the same combination of canonical structure types as the subject antibody are identified to form a candidate set of human sequences. In preferred embodiments, only the peptide sequences of human germline immunoglobulin VH and Vk gene fragments are considered for comparison. Most of these gene fragments have been discovered and have already been assigned to a canonical structure type (Chothia et al, 1992, Tomlinson et al, 1995). Additional V gene fragments not disclosed by these references are provide herein and appear among those sequences listed in FIG. 1 and FIG. 2. For the heavy chain, conformity of CDR1 and CDR2 to the mouse canonical structure types is assessed, and genes that do not conform are excluded. For the light chain, conformity of CDR1 and CDR2 of each human sequence to the canonical structure types of the subject antibody is first assessed. The potential of residues 89-95 of a candidate Vk gene to form a CDR3 of the same canonical structure type as the subject antibody is assessed, by positing a fusion of the gene with a J region and a applying criteria for CDR3 canonical CDR structure type determination to the fused sequence, and non conforming sequences are excluded.

In another embodiment, appropriate when a variable domain of the subject antibody is of a canonical structure type not available in the human genome, human germline V genes that have three-dimensionally similar, but not identical, canonical structure types are considered for comparison. Such a circumstance often occurs with kappa chain CDR1 in murine antibodies, including two of the examples described below. All 6 possible canonical structure types have been observed at this CDR in murine antibodies, whereas the human genome encodes only canonical types 2, 3, 4 and 6. In these circumstances, a canonical CDR structure type having length of amino acid residues within two of the length of the amino acid residues of the subject non-human sequence may selected for the comparison. For example, where a type 1 canonical structure is found in the subject antibody, human Vk sequences with canonical structure type 2 should be used for comparison. Where a type 5 canonical structure is found in the murine antibody, human Vk sequences with either canonical structure type 3 or 4 should be used for comparison.

In another embodiment, mature, rearranged human antibody sequences can be considered for the sequence comparison. Such consideration might be be warranted under a variety of circumstances, including but not limited to instances where the mature human sequence (1) is very close to germline; (2) is known not to be immunogenic in humans; or (3) contains a canonical structure type identical to that of the subject antibody, but not found in the human germline.

In preferred embodiments, for each of the candidate V genes with matching canonical structure types, residue to residue sequence identity and/or homology with the subject sequence is also evaluated to rank the candidate human sequences. In a specific embodiment, the residues evaluated are as follows.:

| Chain | CDR | Residue positions |
|-------|-----|-------------------|
| Kappa | 1 | 26-32 |
| " | 2 | 50-52 |
| " | 3 | 91-96 |
| Heavy | 1 | 31-35 |
| " | 2 | 50-60 |

In preferred embodiments, residue-to-residue homology is first scored by the number of identical amino acid residues between the subject and the candidate human sequences. The human sequence used for subsequent construction of a converted antibody is chosen from among the 25 percent of candidates with the highest score. In other embodiments, appropriate when several candidate sequences have similar identity scores, similarity between non-identical amino acid residues may be additionally be considered. Aliphatic-with-aliphatic, aromatic-with-aromatic, or polar-with-polar matches between subject and object residues are added to the scores. In another embodiment, quantitative evaluation of sequence homology may be performed using amino acid substitution matrices such as the BLOSUM62 matrix of Henikoff and Henikoff (1992).

An object sequence for the framework region C-terminal to CDR3 sequence is selected from the set of known human germline J segments. A preferred J peptide sequence is selected by evaluating residue to residue homology for each J segment for sequence positions for which CDR3 and J overlap, using the scoring criteria specified for the evaluation of candidate V genes as mentioned above. The J gene segment peptide sequence used for subsequent construction of a converted antibody is chosen from among the 25 percent of candidates with the highest score.

In one embodiment, the chimeric variable chain contains at least two CDRs from the subject non-human sequence, and framework sequences from the candidate human sequence. In other embodiments, a chimeric light chain contains three CDRs from the subject non-human sequence and framework sequences from the candidate human sequence. In other embodiments, a chimeric heavy chain contains at least two CDRs of the subject heavy chain, and framework sequence of the candidate human heavy chain. In another embodiment, a chimeric heavy chin contains each of the CDRs from the subject heavy chain and the framework sequences of the candidate human heavy chain. In still another embodiment, a chimeric antibody heavy chain contains CDRs 1 and 3 from the subject non-human sequence and residues 50-60 for CDR2 and residues 61-65 of CDR2 from the candidate human heavy chain, along with the framework sequences of the candidate human sequence. In another embodiment, a chimeric heavy chain sequence contains each CDR from the subject non-human sequence, frameworks sequences 27-30 form the subject sequence, and the framework sequences from the candidate sequences. In all cases however, the chimeric antibody molecule contains no more than 10 amino acid residue in the framework sequence that differ from those in the framework sequence of the candidate human variable region.

In another embodiment, appropriate when increased affinity of a humanized antibody is desired, residues within the CDRs of a converted antibody may be additionally substituted with other amino acids. Typically, no more than four amino acid residues in a CDR are changed, and most typically no more than two residues in the CDR will be changed, except for heavy chain CDR2, where as many as 10 residues may be changed. Similarly, in certain embodiments, some of the amino acids in the framework sequences may be changed. In all embodiments, no more than 10 amino acid residues are changed.

The humanized antibody sequence is then physically assembled by methods of gene synthesis and recombinant protein expression known by those skilled in the art. The final form of the humanized sequences having the chimeric variable chains made by the methods disclosed herein may take many forms. Most typically, the chimeric antibodies will be made by construction a nucleic acid sequence encoding the chimeric variable chains, which are recombinantly expressed in a suitable cell type. One of most typical forms of the chimeric antibody will be an Fab antibody fragment. Other suitable forms of the chimeric antibody include (Fab) 2 molecule, or a single chain Fv molecule. Still other forms may include further fusion to constant domains of a human antibody to form a complete antibody. In preferred embodiments, both light and heavy variable chains are humanized. However, in other embodiment the variable light and heavy chains may be of mixed, i.e., with one fully mouse variable chain (either heavy or light) and the other being a humanized variable chain.

In most embodiments, the method will include screening candidate chimeric antibodies to select those having a dissociation constant for the antigen suitable for an intended use. In most embodiments the humanized antibody made according to these methods will have a dissociation constant of at least about $10^6$ $M^{-1}$, at least about $10^7$ $M^{-1}$ or at least about $10^8$ $M^{-1}$. A Kd of at least about $10^8$ $M^{-1}$ is preferred for most therapeutic uses.

The following Examples illustrate the present invention by showing specific embodiments for humanized antibodies that bind different types of antigens for purposes of illustration. One of ordinary skill in the art will understand that many other specific embodiments may be created using the methods disclosed herein, and that the present invention is not limited by the specific examples.

EXAMPLE 1

Humanized Anti-Chicken Lysozyme

The mouse antibody D1.3 binds to a chicken lysozyme antigen. The peptide sequence of the variable domains of D1.3 were obtained from the Protein Data Bank, accession number 1VFA. The light chain was numbered according to Kabat, and the mouse CDRs were assigned canonical structure types as follows:

Light chain CDR1, numbered according to Kabat, consists of the sequence:

```
                        (Residues 24-34 of SEQ ID NO:94)
24 25 26 27 28 29 30 31 32 33 34
R  A  S  G  N  I  H  N  Y  L  A
```

Because there are no insertions or deletions between residues 27 and 31, CDR1 has canonical structure type 2.

Light chain CDR2, numbered according to Kabat, consists of the sequence:

```
                   (Residues 50-56 of SEQ ID NO:94)
50 51 52 53 54 55 56
Y  T  T  T  L  A  D
```

This is not an exceptional sequence; its canonical structure type is type 1.

Light chain CDR3, numbered according to Kabat, consists of the sequence:

```
                      (Residues 89-97 of SEQ ID NO:94)
89 90 91 92 93 94 95 96 97
Q  H  F  W  S  T  P  R  T
```

Because of the length and the Pro at position 95, this sequence is consistent with canonical structure type 1.

Figure 2:
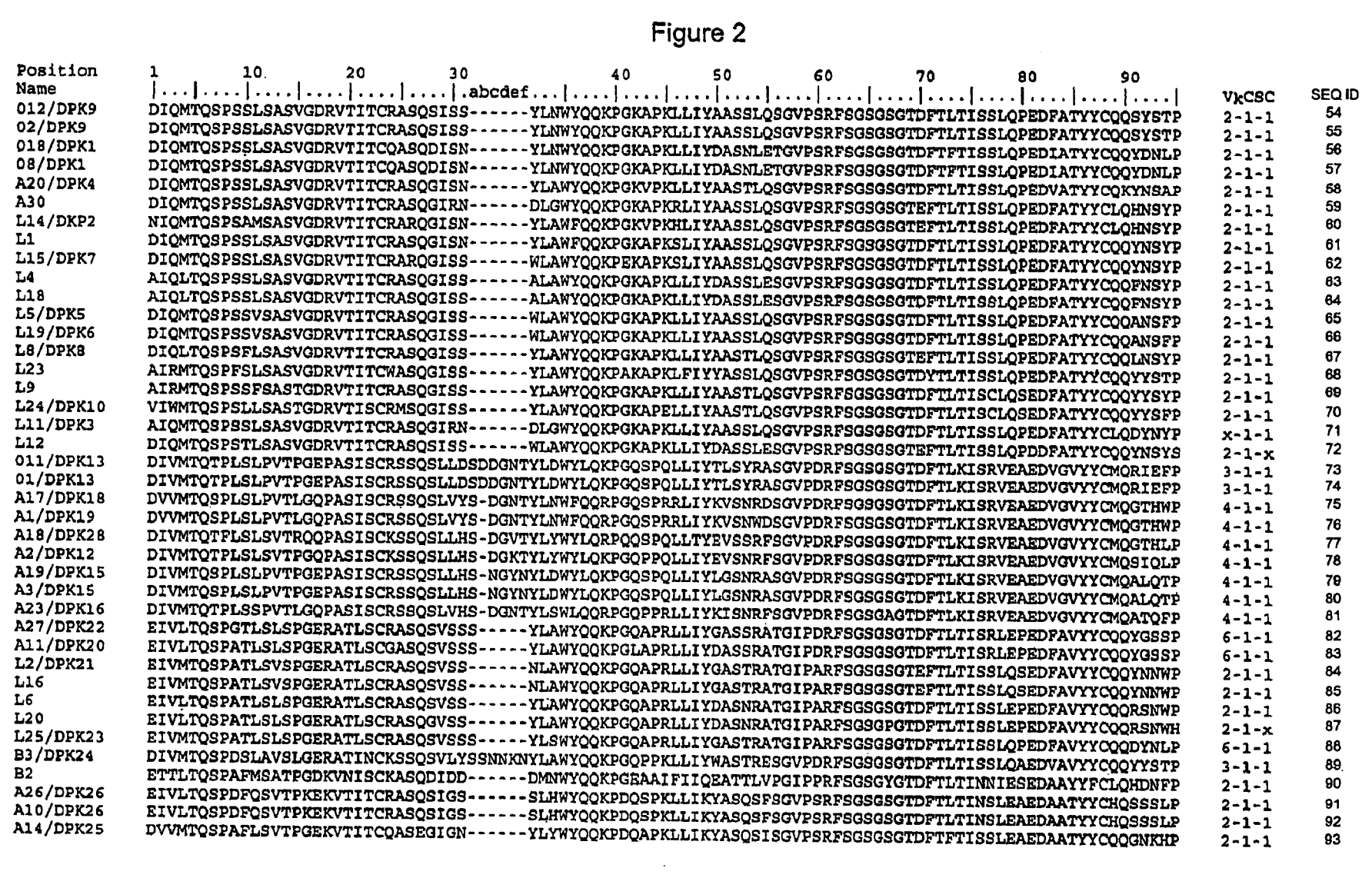

In the compilation in FIG. 2 (SEQ ID NOS:54-93) and in Tomlinson et al (1995), 21 non-redundant human germline Vk genes encode (1) CDR1 with canonical structure type 2, (2) CDR2 with canonical structure type 1, and (3) a sequence with the potential to form canonical structure type 1 at CDR3. These are listed in FIG. 3 (SEQ ID NOS:94-99 and residues 26-32, 50-52, and 9 1-95 of SEQ ID NOS:54, 57, 59-65, 67-72, 84-86, 90, 91, and 93) underneath the D1.3 Vk sequence (SEQ ID NO:94). Their sequence at the residue positions comprising the Chothia canonical structure types is also given, and the human Vk genes in FIG. 3 (SEQ ID NOS:54, 57, 59-65, 67-72, 84-86, 90, 91, and 93) are stratified according to number of residue-to-residue identities in these sequences. L23 has 7 identities, whereas the next three entries on the list have 6. Furthermore, L23 has conserved residues positions 91 and 92, within CDR3, again superior to the next three candidates. L23 therefore is chosen for the humanizing construction.

Among the human Jk segments in FIG. 3 (SEQ ID NOS: 95-99), none matches the Arg in D1.3 at position 96 (SEQ ID NO:94), and all are identical in the next three positions. Jk4, which replicates the GGG motif in D1.3 positions 99-101, is the best match for J segment, and is used for the humanizing construction.

The heavy chain variable domain of D1.3 was numbered according to Kabat, as shown in FIG. 4. CDRs were assigned canonical structure types as follows.

The sequence in the region of the heavy chain CDR1 is

```
                      (Residues 25-35 of SEQ ID NO:100)
27 28 29 30 31 32 33 34 35
F  S  L  T  G  Y  G  V  N
```

This sequence lacks any inserted residues, hence is assigned to canonical structure type 1.

The Kabat CDR2 of D1.3 has the sequence

```
                                (Residues 50-65 of SEQ ID NO:100)
50 51 52 53 54 55 56 57 58 59 60 61 62 63 64 65
M  I  W  G  D  G  N  T  D  Y  N  S  A  L  K  S
```

Because there is no insertion between residues 52 and 56, CDR2 is assigned canonical structure type 1. Human germline VH genes predicted to have canonical structure type 1 at CDR1 and canonical structure type 1 at CDR2 were taken from Chothia et al (1992) and FIG. 1, and are listed in FIG. 4 (residues 27-35 and 50-65 of SEQ ID NOS:18, 29, 40, 42, 48-53, 101).

Segments chosen for homology evaluation were 27-35, corresponding to Kabat CDR1 plus additional residues forming the Chothia canonical structure, and 50-60, corresponding to Kabat CDR2 less residues 61-65, which seldom participate directly in antigen binding. The first two entries have have 8 identities in these segments when compared to the mouse sequence, and the next five have 7 identities. The leading 25% of entries in the similarity ranking are thus the two genes with 8 identities and any of those with seven. Though any of these seven genes would be suitable candidates for a humanizing construction, several are preferred because of conservation in non-identical residues. Three that have Glu or Arg replacing Met at residue 50 are excluded because burial of a charged side chain in the middle of a hydrophobic segment is likely to give an altered three-dimensional structure. V71-4 was thus chosen from the remaining four.

JH4 is clearly the best match to the C terminal end of CDR3.

A chimeric humanized antibody was designed by combining the Kabat CDRs of D1.3 with the Kabat frameworks encoded by V71-4, JH4, L23, and Jk4. The sequences of the heavy and light chain variable domains of this antibody are shown in FIG. 5 (SEQ ID NOS:94, 100, 111, 112).

Figure 6:
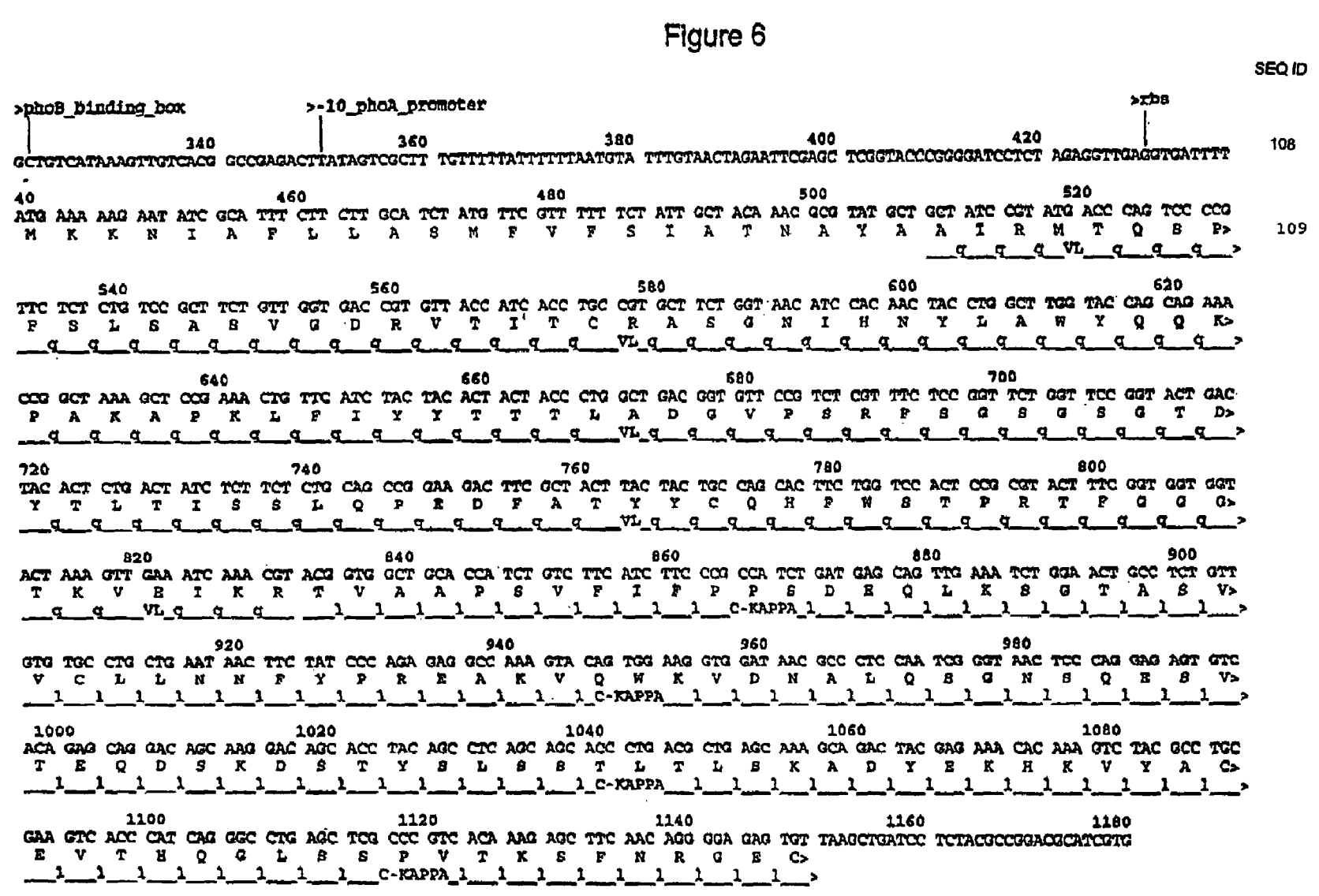

Synthetic variable domain genes encoding the humanized Vk and VH were prepared from synthetic oligonucleotides by the method of Ye et al (1992), incorporated herein by reference. These genes were then transferrred to the Fab expression vector pAK19, described by Carter et al (1992), incorporated herein by reference. The DNA sequence of the synthetic genes and of the Fab expression cassette of pAK19 are shown in FIG. 6 and 6A (SEQ ID NOS:108-110). Recombinant Fab was expressed in E. coli, released from the periplasm by osmotic shock, and purified by chromatography on lysozyme-Sepharose.

The affinity of SHuD1.3 for lysozyme was determined by the fluorescence quench method described in by Foote and Winter (1992). This method relies on changes in the intrinsic tryptophan fluorescence of the antibody and antigen upon complex formation. In the experiment in FIG. 7, 200 nM humanized D1.3 Fab was titrated with small aliquots of a concentrated lysozyme solution. Fluorescence data were fit by least squares to a titration equation to obtain a value and standard error for the dissociation constant, 23±5 nM. By comparison, the Kd of D1.3 IgG is known to have a Kd of 4 nM (Foote and Winter, 1992). Thus the humanized antibody in example 1 has an identical antigenic specificity as the subject mouse antibody, and binds antigen with an affinity diminished by less than a factor of 6 relative to the subject antibody.

EXAMPLE 2

Humanized Anti Human CD28

The mouse anti-human CD28 antibody designated 9.3 was used as the non-human subject antibody. The mouse 9.3 hybridoma line was isolated and is described by Hansen et al (1980).

The heavy and light chain variable region genes of 9.3 were cloned by reverse transcription and the polymerase chain reaction, starting with messenger RNA that had been isolated by a guanidinium isothiocyanate procedure (Chomczynski and Sacchi, 1987) followed by chromatography on oligo-dT columns. Amplification was primed using oligonucleotides complementary to the constant region and oligonucleotides corresponding to regions of the signal peptide or N-terminal framework sequence.

The light chain was numbered according to Kabat, and CDRs were assigned canonical structures types as follows, with reference to FIG. 8.

Light chain CDR1, numbered according to Kabat, consists of the sequence

```
                      (Residues 24-34 of SEQ ID NO:113)
    24 25 26 27 a b c d 28 29 30 31 32 33 34
     R  A  S  E  S V E Y  Y  V  T  S  L  M  Q
```

Because of the inserted residues between 27 and 31, CDR1 has canonical structure type 5.

Light chain CDR2, numbered according to Kabat, consists of the sequence

```
                      (Residues 50-56 of SEQ ID NO:113)
         50 51 52 53 54 55 56
          A  A  S  N  V  E  S
```

This is not an exceptional sequence; its canonical structure type is 1.

Light chain CDR3, numbered according to Kabat, consists of the sequence

```
                      (Residues 89-96 of SEQ ID NO:113)
         89 90 91 92 93 94 95 96
          Q  Q  S  R  K  V  P  Y
```

Because of the length and the Pro at position 95, this sequence is consistent with canonical structure type 1.

Vk sequences with canonical structure type 5 at CDR1 are not represented in the human germline, but structures 3 and 4 resemble canonical structure type 5, and were considered further.

In the compilation in FIG. 2 (SEQ ID NOS:54-93), eight non-redundant human germline Vk genes encode (1) CDR1 with canonical structure type 3 or 4, (2) CDR2 with canonical structure type 1, and (3) a sequence with the potential to form canonical structure type 1 at CDR3. These are listed in FIG. 8 (residues 24-34, 50-56, and 89-95 of SEQ ID NOS:73, 75-79, 81, 89) underneath the 9.3 Vk sequence (SEQ ID NO:113). Their sequence at the Kabat CDR is also given. The human Vk genes in FIG. 3 are ranked according to number of residue-to-residue identities in residue positions forming the Chothia canonical structure. The B3 gene has 7 identities in these position, whereas the next three on the list have 5, hence B3 was chosen for the humanizing construction. Had the scoring been based on Kabat CDR positions, rather than Chothia, B3 would still have been the leading candidate. The 5'-encoded Tyr residue of human Jk2 matched the corresponding position of 9.3 exactly, hence this germline fragment was used.

The heavy chain variable domain of 9.3 was numbered according to Kabat, as shown in FIG. 9 (SEQ ID NO:114). CDRs were assigned canonical structure types as follows.

The sequence in the region of heavy chain CDR1 is

```
                      (Residues 27-35 of SEQ ID NO:114)
         27 28 29 30 31 32 33 34 35
          F  S  L  S  D  Y  G  V  H
```

This sequence lacks any inserted residues, hence is assigned to canonical structure type 1.

The Kabat CDR2 of 9.3 has the sequence

```
                      (Residues 50-65 of SEQ ID NO:114)
50 51 52 53 54 55 56 57 58 59 60 61 62 63 64 65
 V  I  W  A  G  G  G  T  N  Y  N  S  A  L  M  S
```

Because there is no insertion between residues 52 and 56, CDR2 is assigned canonical structure type 1.

Human germline VH genes predicted to have canonical structure type 1 at CDR1 and canonical structure type 1 at CDR2 were taken from Chothia et al (1992) and FIG. 1 (SEQ ID NOS:1-53), and are listed in FIG. 9 (SEQ ID NOS:102-107, residues 27-35 and 50-56 of SEQ ID NOS:18, 29, 40, 42, 48-53, 100).

Segments chosen for homology evaluation were 27-35, corresponding to Kabat CDR1 plus additional residues forming the Chothia canonical structure, and 50-60, corresponding to Kabat CDR2 less residues 61-65, which seldom participate directly in antigen binding. Sequences were scored for number of identical residues when compared to 9.3, and are ranked by score in FIG. 9. Gene DP-45 has the highest number of identities, 10, in a residue-to-residue comparison with 9.3; the next 6 entries all have 9. DP-45 was chosen for the humanizing construction.

Of the human JH segments, JH4 had the closest homology to the C-terminal end of CDR3 in 9.3, hence was used in the construction.

Chimeric humanized antibody variable domains were designed by combining sequences as follows. The light chain variable domain consisted of Kabat CDR sequences of the 9.3 light chain, with the exception of Residue 34, which was thought to be not critical to antigen recognition, hence was made Ala, identical to the residue in B3 at that position; and framework sequences identical to B3 through residue 88 and identical to Jk2 from positions 98-108, with the exception of residues 70 and 72, which were left identical to 9.3 to preserve a glycosylation motif that these residues form in combination with residue 71. The heavy chain variable domain consisted of Kabat CDR sequences of the 9.3 heavy chain, with the exception of residues 60-65, which were thought to be not critical to antigen recognition and hence made identical to the sequence of DP-45 at those positions; and Kabat framework sequences identical to DP-45 through residue 94 and identical to JH4 from residue 103-113.

The sequences of the heavy and light chain variable domains of this antibody are shown in FIG. 10 (SEQ ID NOS:113-116). A recombinant Fab fragment with variable domains these sequences was prepared as described for Example 1, with the exception of using affinity chromatography on Protein-G Sepharose for purification. As a control, a Fab fragment comprised of mouse 9.3 variable domains and human constant domains was prepared by similar methods, as was a hybrid Fab fragment comprised of human constant domains, mouse 9.3 heavy chain variable domain, and humanized light chain variable domain.

Figure 11:
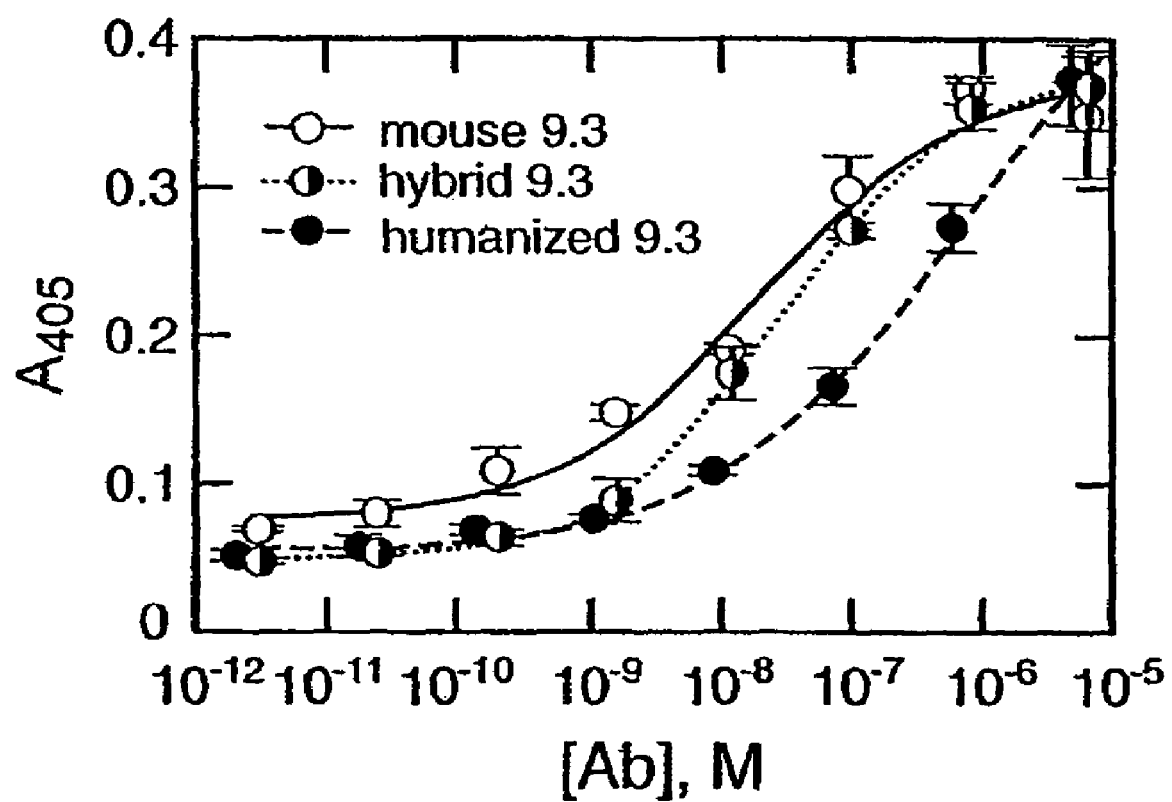
FIG. 11 is a graph that illustrates antigen binding by Hu9.3 Fab fragment, which has an affinity constant of greater than $10^6$ $M^{-1}$, illustrating one embodiment of the invention.
Figure 14:
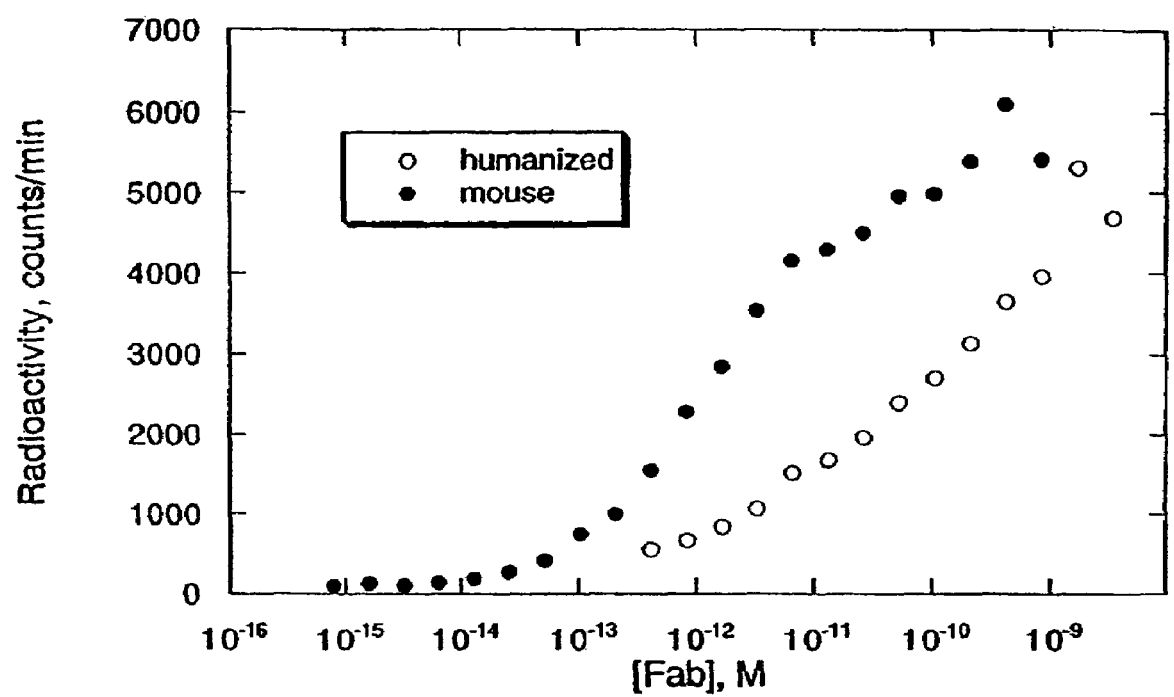
FIG. 14 is a graph that illustrates antigen binding by the humanized anti GAD65 Fab fragment, which has an affinity constant of greater than $10^{11}$ $M^{-1}$, illustrating one embodiment of the invention.

The ability of the three Fabs to bind to CD28 was examined by ELISA. CD28Ig coated plates were incubated with Fab solutions at concentrations ranging from 1 pM to 10 mM. Binding was then assayed with an anti-human k immunoconjugate. The binding isotherms generated were processed to determine the equivalent concentration for half-maximal binding of the antibodies to CD28Ig (EC50) as described in Jin et al (1992), incorporated herein by reference. This analysis, shown in FIG. 11, indicated that the mouse Fab had an EC50 of 20 nM, the EC50 of Hu9.3 was 630 nM, and the EC50 of the hybrid Fab was 30 nM. The similarity of the avidities of the hybrid and mouse Fabs showed that the reduction in binding by humanized 9.3 could be attributed to weakened interactions involving the heavy chain; thus humanization of the light chain alone caused minimal avidity loss.

EXAMPLE 3

Humanized Anti Scorpion Toxin

The mouse anti-scorpion toxin antibody designated BCF2 was used as the subject non-human sequence for a humanized anti-scorpion toxin. The mouse BCF2 hybridoma line was described, and the efficacy of the BCF2 antibody in a mouse model demonstrated by Licea et al (1996). The sequence of the variable domains of BCF2 was disclosed by Selisko et al (1999), and is presented in FIG. 12 (SEQ ID NOS:117-120).

Canonical structure types of the light chain were determined as described before, and were type 5 for CDR1, type 1 for CDR2, and type 1 for CDR3. Canonical structure types of the heavy chain CDRs are type 1 for CDR1 and type 2 for CDR2. A humanized version of BCF2 was designed using the considerations discussed above for selection of human germline V and J gene sequences.

The light chain variable domain consisted of Kabat CDR sequences of the BCF2 light chain; and framework sequences identical to the human gene A2/DPK12 through residue 88 and identical to Jk4 from positions 98-108. The heavy chain variable domain consisted of Kabat CDR sequences of the BCF2 heavy chain, with the exception of residues 62-65, which were thought to be not critical to antigen recognition and hence made identical to the sequence of 1-f/DP3 at those positions; and Kabat framework sequences identical to 1-f/DP3 through residue 94 and identical to JH6 from residue 103-113.

The sequences of the heavy and light chain variable domains of humanized BCF2 antibody are shown in FIG. 12 (SEQ ID NOS:118, 120). A recombinant Fab fragment with variable domains having these sequences was prepared as described for Example 2. As a control, a (Fab)'$_2$ fragment was prepared pepsin digestion of mouse BCF2 IgG obtained from hybridoma cells.

The ability of the two Fabs to bind to CD28 was examined using a BIAcore biosensor instrument, with toxin immobilized on the surface of the sensor chip and antibody in the supernatant. This method has been described by Jönsson et al (1991), incorporated herein by reference. Fab solutions at concentrations varying over at least a 10-fold range were then passed over the chip to observe the association phase. The sensorgram was continued with buffer alone in the fluid phase to observe dissociation. Affinity, as a dissociation equilibrium constant Kd, was determined from the ratio of the kinetic rate constants kon/koff. The respective affinities were 10 nM for the mouse (Fab)'2 and 140 nM for the humanized version.

EXAMPLE 4

Humanized Anti-Human Gad65

The mouse antibody to human glutamic acid decarboxylase 65 kilodalton isoform, NGAD65.

The mouse NGAD65 hybridoma line and sequences of its antibody variable domains were described by Hampe et al (2001) and the sequences are presented in FIG. 13 (SEQ ID NOS:121-124). The first two residues of the light chain are omitted because they were derived from the oligonucleotide used for cloning.

Canonical structure types of the light chain CDRs were determined to be type 4 for CDR1, type 1 for CDR2, and type 1 for CDR3. Canonical structure types of the heavy chain CDRs were determined to be type 1 for CDR1 and type 2 for CDR2.

A humanized version of NGAD65 was designed using the considerations discussed above for selection of human germline V and J gene sequences. The light chain variable domain consisted of Kabat CDR sequences of the NGAD65 light chain; and framework sequences identical to the human Vk gene A17/DPK18 through residue 88 and identical to Jk3 from positions 98-108. The heavy chain variable domain consisted of Kabat CDR sequences of the BCF2 heavy chain, with the exception of residues 61-65, which were thought to be not critical to antigen recognition and hence made identical to the sequence of 1-v at those positions; and Kabat framework sequences identical to 1-f/DP3 through residue 94 and identical to JH4 from residue 103-113.

The sequences of the heavy and light chain variable domains of humanized NGAD65 antibody are shown in FIG. 13 (SEQ ID NOS:122, 124). A recombinant Fab fragment with variable domains having these sequences was prepared as described for Example 2. As a control, a Fab fragment comprised of mouse NGAD65 variable and constant domains was prepared by similar methods.

The ability of the two Fabs to bind to antigen was examined by an immunoprecipitation assay. Radioactive human glutamic acid decarboxylase was prepared by in vitro translation with 35S-methionine. The labeled antigen was incubated overnight with various concentrations of either of the two Fab fragments. Protein G-Sepharose beads were then added to sequester Fab and any associated antigen. Radioactivity was determined by scintillation counting and the EC50 was determined visually from the midpoint of plots of bound radioactivity versus concentration of Fab fragment. Values of EC50 were obtained of 0.36 pM for the mouse Fab and 9 pM for the humanized Fab. Even given the 25-fold loss of affinity of the humanized antibody relative to the mouse antibody, the humanized will still bind antigen sufficiently to be used in human in therapy without need for further mutagenesis of the sequence to make up for the 25 fold loss in affinity.

The methods provided herein have been exemplified by the use of mouse mature antibody genes as a source of the first Chothia canonical CDR and human antibody genes as a source for the second Chothia canonical CDR. These examples are particularly suitable for the construction of humanized antibodies for use in human therapeutic applications. Such humanized antibodies contain sufficient mouse amino sequences to retain a three dimensional structure necessary for avid antigen binding but also contain sufficient human antibody sequences to prevent unwanted immunogenicity in humans. One of ordinary skill in the art will appreciate, however, that the methods disclosed herein are equally applicable to preparing converted antibodies that include chimeric hypervariable regions derived from any two different vertebrate species.

In a more general sense, the first antibody sequence, which is originally selected by virtue of its binding to an antigen, may be referred to as the "subject" antibody sequence. Typically the subject antibody sequence is of mouse or rat origin. The second antibody sequence, which is selected from antibody sequences of the target animal, may be referred to as the "object" antibody sequence. The object antibody sequence is typically from a human or a farm animal that is the object of therapeutic treatment. Antibody compositions containing chimeric hypervariable regions according to the methods of this invention result in a third antibody sequence which may be generally designated a "converted" antibody sequence. The converted antibody sequence differs in certain defined structural features from each of the subject and the object antibody sequences and is identical in certain other defined structural features to each of the subject or object sequences.

REFERENCES

Carter, P., Kelley, R. F., Rodrigues, M. L., Snedecor, B., Covarrubias, M., Velligan, M. D., Wong, W. L. T., Rowland, A. M., Kotts, C. E., Carver, M. E., Yang, M., Bourell, J. H., Shepard, H. M. & Henner, D. (1992) High level *Escherichia coli* expression and production of a bivalent humanized antibody fragment. Bio/Technology 10, 163-167.

Chothia, C. & Lesk, A. M. (1987) Canonical structure types for the hypervariable regions of immunoglobulins. J. Mol. Biol. 96, 901-917.

Chothia, C., Lesk, A. M., Gherardi, E., Tomlinson, I. M., Walter, G., Marks, J. D., Llewelyn, M. B. & Winter, G. (1992) Structural repertoire of the human VH segments. J. Mol. Biol. 227, 799-817.

Chomczynski, P. & Sacchi, N. (1987) Single-step method of RNA isolation by acid guanidinium thiocyanate-phenol-chloroform extraction. Anal. Biochem. 162, 156-159.

Foote, J. & Winter, G. (1992) Antibody residues affecting conformation of the hypervariable loops. J. Mol. Biol. 224, 487499.

Hampe, C. S., Lundgren, P., Daniels, T. L., Hammerle, L. P., Marcovina, S. M. & Lernmark, A. (2001) A novel monoclonal antibody specific for the N-terminal end of GAD65. J Neuroimmunol. 113, 63-71.

Hansen, J. A., Martin, P. J. & Nowinski, R. C. (1980) Monoclonal antibodies identifying a novel T cell antigen and Ia antigens of human lymphocytes. Immunogenetics 10, 247-260.

Jin, L., Fendly, B. M. & Wells, J. A. (1992) High resolution functional analysis of antibody-antigen interactions. J. Mol. Biol. 226, 851-865.

Jones, P. T., Dear, P. H., Foote, J., Neuberger, M. S. & Winter, G. (1986) Replacing the complementarity-determining regions in a human antibody with those from a mouse. Nature 321, 522-525.

Jönsson, U., Fägerstam, L., Ivarsson, B., Lundh, K., Löfås, S., Persson, B., Roos, H., Rönnberg, I., Sjölander, S., Stenber, E., Ståhlberg, R., Urbaniczky, C., Östlin, H. & Malmqvist, M. (1991) Real-time biospecific interaction analysis using surface plasmon resonance and a sensor chip technology. BioTechniques 11, 620-627.

Kabat, E. A., Wu, T. T., Perry, H. M., Gottesman, K. S. & Coeller, K. (1991) Sequences of proteins of immunological interest. 5th ed. 1991, Bethesda: US Dept. of Health and Human Services, PHS, NIH.

Licea, A. F., Becerril, B. & Possani, L. D. (1996) Fab fragments of the monoclonal antibody BCF2 are capable of neutralizing the whole soluble venom from the scorpion Centruroides noxius Hoffman. Toxicon 34, 843-847.

MacCallum, R. M., Martin, A. C. R. & Thornton, J. M. (1996) Antibody-antigen interactions: contact analysis and binding site topography. J. Mol. Biol. 262, 732-745.

Padlan. E. (1991) A possible procedure for reducing the immunogenicity of antibody variable domains while preserving their ligand binding properties, Molecular Immunology 28:489-498

Padlan, E. O., Abergel, C. & Tipper, J. P. (1995) Identification of specificity-determining residues in antibodies. FASEB J. 9, 133-139.

Riechmann, L., Clark, M., Waldmann, H. & Winter, G. (1988) Reshaping human antibodies for therapy. Nature 332, 323-327.

Rutgeerts, P., et al (1999) Efficacy and safety of retreatment with anti-tumor necrosis factor antibody (INFLIXIMAB) to maintain remission in Crohn's disease. Gastroenterology 117, 761-769

Selisko, B., Licea, A. F., Becerril, B., Zamudio, F., Possani, L. D. & Horjales, E. (1999) Antibody BCF2 against scorpion toxin Cn2 from Centruroides noxius Hoffman: primary structure and three-dimensional model as free Fv fragment and complexed with its antigen. Proteins 37, 130-143.

Tamura, M., Milenic, D., Iwahashi, M., E., P., Schlom, J. & Kashmiri, S. (2000) Structural Correlates of an Anticarcinoma Antibody: Identification of Specificity-Determining Residues (SDRs) and Development of a Minimally Immunogenic Antibody Variant by Retention of SDRs Only. J. Immunol. 164, 1432-1441.

Tomlinson, I. M., Cox, J. P. L., Gherardi, E., Lesk, A. M. & Chothia, C. (1995) The structural repertoire of the human Vk domain. EMBO J. 14, 4628-4638.

Wu, T. T. & Kabat, E. A. (1970) An analysis of the sequences of the variable regions of Bence Jones proteins and myeloma light chains and their implications for antibody complementarity. J. Exp. Med. 132, 211-250.

Ye, Q.-Z., Johnson, L. L. & Baragi, V. (1992) Gene synthesis and expression in E. coli for PUMP, a human matrix metalloproteinase. Biochem. Biophys. Res. Comm. 186, 143-149. Martin, A. C. R. & Thornton, J. M. (1996) Structural families in loops of homologous proteins: automatic classification, modelling and application to antibodies. J. Mol. Biol. 263, 800-815.

Henikoff, S. & Henikoff, J. G. (1992) Amino acid substitution matrices from protein blocks. Proc. Natl. Acad. Sci. USA 89, 10915-10919.

---

The invention claimed is:

1. A humanized antibody or a binding fragment thereof comprising:

a humanized heavy chain variable region containing three CDR sequences from a heavy chain variable region of a subject non-human antibody grafted into a variable region framework of a candidate human germline heavy chain variable region sequence and comprises two human CDR sequences with the same canonical structure type as the non-human CDR sequences in the subject non-human antibody for two corresponding CDR positions, provided that residues 61-65 of CDR2 of the humanized heavy chain variable region are residues from positions 61-65 from the candidate human germline heavy chain variable region sequence; and a humanized light chain variable region containing three CDR sequences from a light chain variable region of the subject antibody grafted into a variable region framework of a candidate human germline light chain variable region sequence and comprises three human CDR sequences with the same canonical structure type as non-human CDR sequences from the subject non-human antibody for three corresponding CDR positions;

wherein the humanized antibody or a binding fragment thereof selected from a Fab fragment, a (Fab)'2 molecule, and a single chain Fv molecule binds to the same antigen as the subject non-human antibody wherein the CDR boundaries and numbering of residues of the humanized antibody are as defined by Kabat.

2. A humanized antibody or binding fragment thereof comprising:

a humanized heavy chain variable region containing three non-human CDR sequences from a non-human heavy chain variable region from a subject non-human antibody grafted into a heavy chain variable region framework sequence that is characterized by having no more than 10 amino acid residues that differ from a framework sequence of a candidate human germline antibody heavy chain variable region sequence and comprises two human CDR sequences with the same canonical structure type as the non-human CDR sequences from the heavy chain variable region of the subject non-human antibody for the two corresponding CDR positions provided that residues 61-65 of CDR2 of the humanized heavy chain variable region are residues from positions 61-65 from the candidate human germline heavy chain variable region sequence; and a humanized antibody light chain variable region containing three non-human CDR sequences from a non-human light chain variable region of the subject non-human antibody grafted into a light chain variable region framework sequence that is characterized by having no more than 10 amino acid residues that differ from a framework sequence of a candidate human germline antibody light chain variable region sequence and comprises two human CDR sequences with the same canonical structure type as the non-human CDR sequences from the light chain variable region of the subject non-human antibody for the two corresponding CDR positions, wherein the humanized antibody or a binding fragment thereof selected from a Fab fragment, a (Fab)'2 molecule, and a single chain Fv molecule binds to the same anantigen as the subject non-human antibody;

wherein the CDR boundaries and numbering of residues of the humanized antibody are as defined by Kabat.

3. The humanized antibody or binding fragment of claim 2, wherein the subject non-human antibody is a mouse antibody.

4. The humanized antibody or binding fragment thereof of claim 2 in the form of a molecule selected from the group consisting of a Fab fragment, a (Fab)'$_2$ molecule, and a single chain Fv molecule.

5. The humanized antibody or binding fragment of claim 2, further comprising a human antibody constant region.

6. The humanized antibody or binding fragment of claim 2 that has an association constant for its antigen of at least $10^6$ $M^{-1}$, at least $10^7$ $M^{-1}$ or at least $10^8$ $M^{-1}$.

7. The humanized antibody or binding fragment of claim 2 that does not elicit an immune response when administered to a human.

8. The humanized antibody or binding fragment of claim 2 that binds a human CD28 antigen.

9. The humanized antibody or binding fragment of claim 2, wherein the heavy chain variable region framework sequence has no more than 2 amino acid residues that differ from the framework sequence of the candidate human antibody heavy chain variable region sequence.

10. The humanized antibody or binding fragment of claim 2, with the proviso that if one of the three non-human light chain CDR sequences does not have the same canonical structure type as the human CDR sequence for the corresponding CDR position of the one CDR, then the differing canonical structure type of the candidate human variable region has a length no more than two amino acid residues smaller or larger than the non-human canonical structure type at the corresponding position.

11. The humanized antibody or binding fragment of claim 10, wherein:

if the one non-human light chain CDR sequence not having the same canonical structure type as the corresponding human CDR is of canonical type 1, then the candidate human variable region has a canonical type 2 CDR at the corresponding position; or if the one non-human CDR sequence is of canonical type 5, then the candidate human variable region has a canonical type 4 or 3 CDR at the corresponding position.

12. The humanized antibody or binding fragment of claim 2, wherein the candidate human antibody germline light chain variable region sequence comprises three human CDR sequences with the same canonical structure type as the non-human CDR sequences for the three corresponding CDR positions.

* * * * *

SEQUENCE LISTING

```
<160> NUMBER OF SEQ ID NOS: 124

<210> SEQ ID NO 1
<211> LENGTH: 98
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 2
<211> LENGTH: 98
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80
```

Met Glu Leu Ser Ser Leu Arg Ser Glu Asp Thr Ala Val Tyr Tyr Cys
            85                  90                  95

Ala Arg

<210> SEQ ID NO 3
<211> LENGTH: 98
<212> TYPE: PRT
<213> ORGANISM: Homo sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
            85                  90                  95

Ala Arg

<210> SEQ ID NO 4
<211> LENGTH: 98
<212> TYPE: PRT
<213> ORGANISM: Homo sapiens

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg

<210> SEQ ID NO 5
<211> LENGTH: 98
<212> TYPE: PRT
<213> ORGANISM: Homo sapiens

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe

```
                50                  55                  60
Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 6
<211> LENGTH: 98
<212> TYPE: PRT
<213> ORGANISM: Homo sapiens

<400> SEQUENCE: 6

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
                20                  25                  30

Tyr Leu His Trp Val Arg Gln Ala Pro Gly Gln Ala Leu Glu Trp Met
            35                  40                  45

Gly Trp Ile Thr Pro Phe Asn Gly Asn Thr Asn Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

<210> SEQ ID NO 7
<211> LENGTH: 98
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 8
<211> LENGTH: 98
<212> TYPE: PRT
<213> ORGANISM: Homo sapiens

<400> SEQUENCE: 8

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
                20                  25                  30
```

Ala Val Gln Trp Val Arg Gln Ala Arg Gly Gln Arg Leu Glu Trp Ile
            35                  40                  45

Gly Trp Ile Val Val Gly Ser Gly Asn Thr Asn Tyr Ala Gln Lys Phe
 50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Ala

<210> SEQ ID NO 9
<211> LENGTH: 98
<212> TYPE: PRT
<213> ORGANISM: Homo sapiens

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg

<210> SEQ ID NO 10
<211> LENGTH: 98
<212> TYPE: PRT
<213> ORGANISM: Homo sapiens

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg

<210> SEQ ID NO 11
<211> LENGTH: 98
<212> TYPE: PRT
<213> ORGANISM: Homo sapiens

<400> SEQUENCE: 11

Glu Val Gln Leu Val Gln Ser Gly Ala Glu Val Lys Pro Gly Ala
1               5                   10                  15

Thr Val Lys Ile Ser Cys Lys Val Ser Gly Tyr Thr Phe Thr Asp Tyr
                20                  25                  30

Tyr Met His Trp Val Gln Ala Pro Gly Lys Gly Leu Glu Trp Met
            35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 12
<211> LENGTH: 100
<212> TYPE: PRT
<213> ORGANISM: Homo sapiens

<400> SEQUENCE: 12

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 13
<211> LENGTH: 100
<212> TYPE: PRT
<213> ORGANISM: Homo sapiens

<400> SEQUENCE: 13

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
                20                  25                  30

Arg Met Gly Val Ser Trp Ile Arg Gln Pro Pro Gly Lys Ala Leu Glu
            35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 14
<211> LENGTH: 100
<212> TYPE: PRT
<213> ORGANISM: Homo sapiens

<400> SEQUENCE: 14

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Asp Lys Phe Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 15
<211> LENGTH: 98
<212> TYPE: PRT
<213> ORGANISM: Homo sapiens

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 16
<211> LENGTH: 99
<212> TYPE: PRT
<213> ORGANISM: Homo sapiens

<400> SEQUENCE: 16

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Leu Tyr Tyr Cys
                85                  90                  95

Ala Lys Asp

<210> SEQ ID NO 17
<211> LENGTH: 98
<212> TYPE: PRT
<213> ORGANISM: Homo sapiens

<400> SEQUENCE: 17

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 18
<211> LENGTH: 97
<212> TYPE: PRT
<213> ORGANISM: Homo sapiens

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met His Trp Val Arg Gln Ala Thr Gly Lys Gly Leu Glu Trp Val
            35                  40                  45

Ser Ala Ile Gly Thr Ala Gly Asp Thr Tyr Tyr Pro Gly Ser Val Lys
        50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 19
<211> LENGTH: 100
<212> TYPE: PRT
<213> ORGANISM: Homo sapiens

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
```

```
                50                  55                  60
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr
            100

<210> SEQ ID NO 20
<211> LENGTH: 98
<212> TYPE: PRT
<213> ORGANISM: Homo sapiens

<400> SEQUENCE: 20

Glu Val Gln Leu Val Glu Ser Gly Gly Gly Val Val Arg Pro Gly Gly
  1               5                  10                  15

Ser Leu Arg Leu Ser Cys Ala Ala Ser Gly Phe Thr Phe Asp Asp Tyr
                 20                  25                  30

Gly Met Ser Trp Val Arg Gln Ala Pro Gly Lys Gly Leu Glu Trp Val
             35                  40                  45

Ser Gly Ile Asn Trp Asn Gly Gly Ser Thr Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Arg

<210> SEQ ID NO 21
<211> LENGTH: 98
<212> TYPE: PRT
<213> ORGANISM: Homo sapiens

<400> SEQUENCE: 21

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
                 20                  25                  30

Ser Met Asn Trp Val Arg Gln Ala Pro Gly Lys Gly Leu Glu Trp Val
             35                  40                  45

Ser Ser Ile Ser Ser Ser Ser Tyr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 22
<211> LENGTH: 98
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
```

-continued

```
                    20                  25                  30
Ala Met Ser Trp Val Arg Gln Ala Pro Gly Lys Gly Leu Glu Trp Val
            35                  40                  45
Ser Ala Ile Ser Gly Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys

<210> SEQ ID NO 23
<211> LENGTH: 98
<212> TYPE: PRT
<213> ORGANISM: Homo sapiens

<400> SEQUENCE: 23

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
                20                  25                  30
Gly Met His Trp Val Arg Gln Ala Pro Gly Lys Gly Leu Glu Trp Val
            35                  40                  45
Ala Val Ile Ser Tyr Asp Gly Ser Asn Lys Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys

<210> SEQ ID NO 24
<211> LENGTH: 98
<212> TYPE: PRT
<213> ORGANISM: Homo sapiens

<400> SEQUENCE: 24

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
                20                  25                  30
Ala Met His Trp Val Arg Gln Ala Pro Gly Lys Gly Leu Glu Trp Val
            35                  40                  45
Ala Val Ile Ser Tyr Asp Gly Ser Asn Lys Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg

<210> SEQ ID NO 25
<211> LENGTH: 98
<212> TYPE: PRT
<213> ORGANISM: Homo sapiens

<400> SEQUENCE: 25
```

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys
```

<210> SEQ ID NO 26
<211> LENGTH: 98
<212> TYPE: PRT
<213> ORGANISM: Homo sapiens

<400> SEQUENCE: 26

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg
```

<210> SEQ ID NO 27
<211> LENGTH: 99
<212> TYPE: PRT
<213> ORGANISM: Homo sapiens

<400> SEQUENCE: 27

```
Glu Val Gln Leu Val Glu Ser Gly Gly Val Val Val Gln Pro Gly Gly
 1               5                  10                  15

Ser Leu Arg Leu Ser Cys Ala Ala Ser Gly Phe Thr Phe Asp Asp Tyr
                20                  25                  30

Thr Met His Trp Val Arg Gln Ala Pro Gly Lys Gly Leu Glu Trp Val
             35                  40                  45

Ser Leu Ile Ser Trp Asp Gly Gly Ser Thr Tyr Tyr Ala Asp Ser Val
         50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Thr Glu Asp Thr Ala Leu Tyr Tyr Cys
                 85                  90                  95

Ala Lys Asp
```

<210> SEQ ID NO 28

-continued

```
<211> LENGTH: 98
<212> TYPE: PRT
<213> ORGANISM: Homo sapiens

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg

<210> SEQ ID NO 29
<211> LENGTH: 97
<212> TYPE: PRT
<213> ORGANISM: Homo sapiens

<400> SEQUENCE: 29

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 30
<211> LENGTH: 98
<212> TYPE: PRT
<213> ORGANISM: Homo sapiens

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Pro Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Gly Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg

<210> SEQ ID NO 31
<211> LENGTH: 97
<212> TYPE: PRT
<213> ORGANISM: Homo sapiens

<400> SEQUENCE: 31

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Val Ser Ser Asn
            20                  25                  30
Tyr Met Ser Trp Val Arg Gln Ala Pro Gly Lys Gly Leu Glu Trp Val
        35                  40                  45
Ser Val Ile Tyr Ser Gly Gly Ser Thr Tyr Tyr Ala Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg

<210> SEQ ID NO 32
<211> LENGTH: 100
<212> TYPE: PRT
<213> ORGANISM: Homo sapiens

<400> SEQUENCE: 32

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp His
            20                  25                  30
Tyr Met Asp Trp Val Arg Gln Ala Pro Gly Lys Gly Leu Glu Trp Val
        35                  40                  45
Gly Arg Thr Arg Asn Lys Ala Asn Ser Tyr Thr Thr Glu Tyr Ala Ala
    50                  55                  60
Ser Val Lys Gly Arg Phe Thr Ile Ser Arg Asp Asp Ser Lys Asn Ser
65                  70                  75                  80
Leu Tyr Leu Gln Met Asn Ser Leu Lys Thr Glu Asp Thr Ala Val Tyr
                85                  90                  95
Tyr Cys Ala Arg
            100

<210> SEQ ID NO 33
<211> LENGTH: 98
<212> TYPE: PRT
<213> ORGANISM: Homo sapiens

<400> SEQUENCE: 33

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Trp Met His Trp Val Arg Gln Ala Pro Gly Lys Gly Leu Val Trp Val
        35                  40                  45
Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 34
<211> LENGTH: 98
<212> TYPE: PRT
<213> ORGANISM: Homo sapiens

<400> SEQUENCE: 34

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 35
<211> LENGTH: 98
<212> TYPE: PRT
<213> ORGANISM: Homo sapiens

<400> SEQUENCE: 35

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
                20                  25                  30

Asn Trp Trp Gly Trp Ile Arg Gln Pro Pro Gly Lys Gly Leu Glu Trp
            35                  40                  45

Ile Gly Tyr Ile Tyr Tyr Ser Gly Ser Thr Tyr Tyr Asn Pro Ser Leu
        50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg

<210> SEQ ID NO 36
<211> LENGTH: 99
<212> TYPE: PRT
<213> ORGANISM: Homo sapiens

<400> SEQUENCE: 36

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

```
Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 37
<211> LENGTH: 99
<212> TYPE: PRT
<213> ORGANISM: Homo sapiens

<400> SEQUENCE: 37

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
            35                  40                  45

Trp Ile Gly Tyr Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 38
<211> LENGTH: 99
<212> TYPE: PRT
<213> ORGANISM: Homo sapiens

<400> SEQUENCE: 38

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 39
<211> LENGTH: 99
<212> TYPE: PRT
<213> ORGANISM: Homo sapiens

<400> SEQUENCE: 39

Gln Val Gln Leu Gln Glu Ser Gly Pro Gly Leu Val Lys Pro Ser Gln
```

```
                 1               5                  10                 15
Thr Leu Ser Leu Thr Cys Thr Val Ser Gly Gly Ser Ile Ser Ser Gly
                20                 25                 30

Gly Tyr Tyr Trp Ser Trp Ile Arg Gln His Pro Gly Lys Gly Leu Glu
                35                 40                 45

Trp Ile Gly Tyr Ile Tyr Tyr Ser Gly Ser Thr Tyr Tyr Asn Pro Ser
                50                 55                 60

Leu Lys Ser Arg Val Thr Ile Ser Val Asp Thr Ser Lys Asn Gln Phe
65                                 70                 75                80

Ser Leu Lys Leu Ser Ser Val Thr Ala Ala Asp Thr Ala Val Tyr Tyr
                85                 90                 95

Cys Ala Arg

<210> SEQ ID NO 40
<211> LENGTH: 97
<212> TYPE: PRT
<213> ORGANISM: Homo sapiens

<400> SEQUENCE: 40

Gln Val Gln Leu Gln Gln Trp Gly Ala Gly Leu Leu Lys Pro Ser Glu
1               5                  10                 15

Thr Leu Ser Leu Thr Cys Ala Val Tyr Gly Gly Ser Phe Ser Gly Tyr
                20                 25                 30

Tyr Trp Ser Trp Ile Arg Gln Pro Pro Gly Lys Gly Leu Glu Trp Ile
                35                 40                 45

Gly Glu Ile Asn His Ser Gly Ser Thr Asn Tyr Asn Pro Ser Leu Lys
                50                 55                 60

Ser Arg Val Thr Ile Ser Val Asp Thr Ser Lys Asn Gln Phe Ser Leu
65                                 70                 75                80

Lys Leu Ser Ser Val Thr Ala Ala Asp Thr Ala Val Tyr Tyr Cys Ala
                85                 90                 95

Arg

<210> SEQ ID NO 41
<211> LENGTH: 99
<212> TYPE: PRT
<213> ORGANISM: Homo sapiens

<400> SEQUENCE: 41

Gln Leu Gln Leu Gln Glu Ser Gly Pro Gly Leu Val Lys Pro Ser Glu
1               5                  10                 15

Thr Leu Ser Leu Thr Cys Thr Val Ser Gly Gly Ser Ile Ser Ser Ser
                20                 25                 30

Ser Tyr Tyr Trp Gly Trp Ile Arg Gln Pro Pro Gly Lys Gly Leu Glu
                35                 40                 45

Trp Ile Gly Ser Ile Tyr Tyr Ser Gly Ser Thr Tyr Tyr Asn Pro Ser
                50                 55                 60

Leu Lys Ser Arg Val Thr Ile Ser Val Asp Thr Ser Lys Asn Gln Phe
65                                 70                 75                80

Ser Leu Lys Leu Ser Ser Val Thr Ala Ala Asp Thr Ala Val Tyr Tyr
                85                 90                 95

Cys Ala Arg

<210> SEQ ID NO 42
<211> LENGTH: 97
<212> TYPE: PRT
```

-continued

<213> ORGANISM: Homo sapiens

<400> SEQUENCE: 42

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 43
<211> LENGTH: 99
<212> TYPE: PRT
<213> ORGANISM: Homo sapiens

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 44
<211> LENGTH: 98
<212> TYPE: PRT
<213> ORGANISM: Homo sapiens

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 45
<211> LENGTH: 98
<212> TYPE: PRT
<213> ORGANISM: Homo sapiens

<400> SEQUENCE: 45

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 46
<211> LENGTH: 101
<212> TYPE: PRT
<213> ORGANISM: Homo sapiens

<400> SEQUENCE: 46

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
            100

<210> SEQ ID NO 47
<211> LENGTH: 98
<212> TYPE: PRT
<213> ORGANISM: Homo sapiens

<400> SEQUENCE: 47

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr

```
Leu Gln Ile Cys Ser Leu Lys Ala Glu Asp Thr Ala Val Tyr Tyr Cys
            85                  90                  95

Ala Arg

<210> SEQ ID NO 48
<211> LENGTH: 97
<212> TYPE: PRT
<213> ORGANISM: Homo sapiens

<400> SEQUENCE: 48

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
            85                  90                  95

Arg

<210> SEQ ID NO 49
<211> LENGTH: 97
<212> TYPE: PRT
<213> ORGANISM: Homo sapiens

<400> SEQUENCE: 49

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Ile His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg

<210> SEQ ID NO 50
<211> LENGTH: 97
<212> TYPE: PRT
<213> ORGANISM: Homo sapiens

<400> SEQUENCE: 50

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Val Ser Gly Tyr
            20                  25                  30

Tyr Trp Ser Trp Ile Arg Gln Pro Pro Gly Lys Gly Leu Glu Trp Ile
        35                  40                  45
```

Gly Tyr Ile Tyr Tyr Ser Gly Ser Thr Asn Asn Pro Ser Leu Lys
    50                  55                  60

Ser Arg Ala Thr Ile Ser Val Asp Thr Ser Lys Asn Gln Phe Ser Leu
65                  70                  75                  80

Asn Leu Ser Ser Val Thr Ala Ala Asp Thr Ala Val Tyr Cys Cys Ala
                85                  90                  95

Arg

<210> SEQ ID NO 51
<211> LENGTH: 97
<212> TYPE: PRT
<213> ORGANISM: Homo sapiens

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Ala Gly Lys Gly Leu Glu Trp Ile
            35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 52
<211> LENGTH: 97
<212> TYPE: PRT
<213> ORGANISM: Homo sapiens

<400> SEQUENCE: 52

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 53
<211> LENGTH: 97
<212> TYPE: PRT
<213> ORGANISM: Homo sapiens

<400> SEQUENCE: 53

Gln Val Gln Leu Gln Glu Ser Gly Pro Gly Leu Val Lys Pro Ser Asp
1               5                   10                  15

```
Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg

<210> SEQ ID NO 54
<211> LENGTH: 95
<212> TYPE: PRT
<213> ORGANISM: Homo sapiens

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
            85                  90                  95

<210> SEQ ID NO 55
<211> LENGTH: 95
<212> TYPE: PRT
<213> ORGANISM: Homo sapiens

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
            85                  90                  95

<210> SEQ ID NO 56
<211> LENGTH: 95
<212> TYPE: PRT
<213> ORGANISM: Homo sapiens

<400> SEQUENCE: 56

Asp Ile Gln Met Thr Gln Ser Pro Ser Ser Leu Ser Ala Ser Val Gly
1               5                   10                  15
```

```
Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 57
<211> LENGTH: 95
<212> TYPE: PRT
<213> ORGANISM: Homo sapiens

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 58
<211> LENGTH: 95
<212> TYPE: PRT
<213> ORGANISM: Homo sapiens

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95

<210> SEQ ID NO 59
<211> LENGTH: 95
<212> TYPE: PRT
<213> ORGANISM: Homo sapiens

<400> SEQUENCE: 59

Asp Ile Gln Met Thr Gln Ser Pro Ser Ser Leu Ser Ala Ser Val Gly
1               5                   10                  15
```

-continued

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 60
<211> LENGTH: 95
<212> TYPE: PRT
<213> ORGANISM: Homo sapiens

<400> SEQUENCE: 60

Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile Ser Asn Tyr
            20                  25                  30

Leu Ala Trp Phe Gln Gln Lys Pro Gly Lys Val Pro Lys His Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 61
<211> LENGTH: 95
<212> TYPE: PRT
<213> ORGANISM: Homo sapiens

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 62
<211> LENGTH: 95
<212> TYPE: PRT
<213> ORGANISM: Homo sapiens

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Gly Ile Ser Ser Trp

-continued

```
                    20                  25                  30

Leu Ala Trp Tyr Gln Gln Lys Pro Glu Lys Ala Pro Lys Ser Leu Ile
                35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 63
<211> LENGTH: 95
<212> TYPE: PRT
<213> ORGANISM: Homo sapiens

<400> SEQUENCE: 63

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
                35                  40                  45

Tyr Asp Ala Ser Ser Leu Glu Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro
                 85                  90                  95

<210> SEQ ID NO 64
<211> LENGTH: 95
<212> TYPE: PRT
<213> ORGANISM: Homo sapiens

<400> SEQUENCE: 64

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
                35                  40                  45

Tyr Asp Ala Ser Ser Leu Glu Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro
                 85                  90                  95

<210> SEQ ID NO 65
<211> LENGTH: 95
<212> TYPE: PRT
<213> ORGANISM: Homo sapiens

<400> SEQUENCE: 65

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30
```

```
Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                 85                  90                  95
```

<210> SEQ ID NO 66
<211> LENGTH: 95
<212> TYPE: PRT
<213> ORGANISM: Homo sapiens

<400> SEQUENCE: 66

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                 85                  90                  95
```

<210> SEQ ID NO 67
<211> LENGTH: 95
<212> TYPE: PRT
<213> ORGANISM: Homo sapiens

<400> SEQUENCE: 67

```
Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro
                 85                  90                  95
```

<210> SEQ ID NO 68
<211> LENGTH: 95
<212> TYPE: PRT
<213> ORGANISM: Homo sapiens

<400> SEQUENCE: 68

```
Ala Ile Arg Met Thr Gln Ser Pro Phe Ser Leu Ser Ala Ser Val Gly
 1               5                  10                  15

Asp Arg Val Thr Ile Thr Cys Trp Ala Ser Gln Gly Ile Ser Ser Tyr
                 20                  25                  30
```

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95

<210> SEQ ID NO 69
<211> LENGTH: 95
<212> TYPE: PRT
<213> ORGANISM: Homo sapiens

<400> SEQUENCE: 69

Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro
                85                  90                  95

<210> SEQ ID NO 70
<211> LENGTH: 95
<212> TYPE: PRT
<213> ORGANISM: Homo sapiens

<400> SEQUENCE: 70

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
                20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Phe Pro
                85                  90                  95

<210> SEQ ID NO 71
<211> LENGTH: 95
<212> TYPE: PRT
<213> ORGANISM: Homo sapiens

<400> SEQUENCE: 71

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile

-continued

```
                35                  40                  45
Tyr Ala Ala Ser Ser Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Leu Gln Asp Tyr Asn Tyr Pro
                 85                  90                  95

<210> SEQ ID NO 72
<211> LENGTH: 95
<212> TYPE: PRT
<213> ORGANISM: Homo sapiens

<400> SEQUENCE: 72

Asp Ile Gln Met Thr Gln Ser Pro Ser Thr Leu Ser Ala Ser Val Gly
 1               5                  10                  15
Asp Arg Val Thr Ile Thr Cys Arg Ala Ser Gln Ser Ile Ser Ser Trp
                 20                  25                  30
Leu Ala Trp Tyr Gln Gln Lys Pro Gly Lys Ala Pro Lys Leu Leu Ile
             35                  40                  45
Tyr Asp Ala Ser Ser Leu Glu Ser Gly Val Pro Ser Arg Phe Ser Gly
         50                  55                  60
Ser Gly Ser Gly Thr Glu Phe Thr Leu Thr Ile Ser Ser Leu Gln Pro
 65                  70                  75                  80
Asp Asp Phe Ala Thr Tyr Tyr Cys Gln Gln Tyr Asn Ser Tyr Ser
                 85                  90                  95

<210> SEQ ID NO 73
<211> LENGTH: 101
<212> TYPE: PRT
<213> ORGANISM: Homo sapiens

<400> SEQUENCE: 73

Asp Ile Val Met Thr Gln Thr Pro Leu Ser Leu Pro Val Thr Pro Gly
 1               5                  10                  15
Glu Pro Ala Ser Ile Ser Cys Arg Ser Ser Gln Ser Leu Leu Asp Ser
                 20                  25                  30
Asp Asp Gly Asn Thr Tyr Leu Asp Trp Tyr Leu Gln Lys Pro Gly Gln
             35                  40                  45
Ser Pro Gln Leu Leu Ile Tyr Thr Leu Ser Tyr Arg Ala Ser Gly Val
         50                  55                  60
Pro Asp Arg Phe Ser Gly Ser Gly Ser Gly Thr Asp Phe Thr Leu Lys
 65                  70                  75                  80
Ile Ser Arg Val Glu Ala Glu Asp Val Gly Val Tyr Tyr Cys Met Gln
                 85                  90                  95
Arg Ile Glu Phe Pro
            100

<210> SEQ ID NO 74
<211> LENGTH: 101
<212> TYPE: PRT
<213> ORGANISM: Homo sapiens

<400> SEQUENCE: 74

Asp Ile Val Met Thr Gln Thr Pro Leu Ser Leu Pro Val Thr Pro Gly
 1               5                  10                  15
Glu Pro Ala Ser Ile Ser Cys Arg Ser Ser Gln Ser Leu Leu Asp Ser
                 20                  25                  30
```

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
            85                  90                  95

Arg Ile Glu Phe Pro
            100

<210> SEQ ID NO 75
<211> LENGTH: 100
<212> TYPE: PRT
<213> ORGANISM: Homo sapiens

<400> SEQUENCE: 75

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr His Trp Pro
            100

<210> SEQ ID NO 76
<211> LENGTH: 100
<212> TYPE: PRT
<213> ORGANISM: Homo sapiens

<400> SEQUENCE: 76

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr His Trp Pro
            100

<210> SEQ ID NO 77
<211> LENGTH: 100
<212> TYPE: PRT
<213> ORGANISM: Homo sapiens

<400> SEQUENCE: 77

Asp Ile Val Met Thr Gln Thr Phe Leu Ser Leu Ser Val Thr Arg Gln
1               5                   10                  15

Gln Pro Ala Ser Ile Ser Cys Lys Ser Gln Ser Leu Leu His Ser
            20                  25                  30

Asp Gly Val Thr Tyr Leu Tyr Trp Tyr Leu Gln Arg Pro Gln Gln Ser
        35                  40                  45

Pro Gln Leu Leu Thr Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Leu Pro
            100

<210> SEQ ID NO 78
<211> LENGTH: 100
<212> TYPE: PRT
<213> ORGANISM: Homo sapiens

<400> SEQUENCE: 78

Asp Ile Val Met Thr Gln Thr Pro Leu Ser Leu Ser Val Thr Pro Gly
1               5                   10                  15

Gln Pro Ala Ser Ile Ser Cys Lys Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 79
<211> LENGTH: 100
<212> TYPE: PRT
<213> ORGANISM: Homo sapiens

<400> SEQUENCE: 79

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 80
<211> LENGTH: 100
<212> TYPE: PRT
<213> ORGANISM: Homo sapiens

<400> SEQUENCE: 80

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 81
<211> LENGTH: 100
<212> TYPE: PRT
<213> ORGANISM: Homo sapiens

<400> SEQUENCE: 81

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro
            100

<210> SEQ ID NO 82
<211> LENGTH: 96
<212> TYPE: PRT
<213> ORGANISM: Homo sapiens

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser

-continued

```
                    50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

<210> SEQ ID NO 83
<211> LENGTH: 96
<212> TYPE: PRT
<213> ORGANISM: Homo sapiens

<400> SEQUENCE: 83

Glu Ile Val Leu Thr Gln Ser Pro Ala Thr Leu Ser Leu Ser Pro Gly
 1               5                  10                  15

Glu Arg Ala Thr Leu Ser Cys Gly Ala Ser Gln Ser Val Ser Ser Ser
                 20                  25                  30

Tyr Leu Ala Trp Tyr Gln Gln Lys Pro Gly Leu Ala Pro Arg Leu Leu
             35                  40                  45

Ile Tyr Asp Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

<210> SEQ ID NO 84
<211> LENGTH: 95
<212> TYPE: PRT
<213> ORGANISM: Homo sapiens

<400> SEQUENCE: 84

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro
                 85                  90                  95

<210> SEQ ID NO 85
<211> LENGTH: 95
<212> TYPE: PRT
<213> ORGANISM: Homo sapiens

<400> SEQUENCE: 85

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60
```

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 86
<211> LENGTH: 95
<212> TYPE: PRT
<213> ORGANISM: Homo sapiens

<400> SEQUENCE: 86

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 87
<211> LENGTH: 95
<212> TYPE: PRT
<213> ORGANISM: Homo sapiens

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95

<210> SEQ ID NO 88
<211> LENGTH: 96
<212> TYPE: PRT
<213> ORGANISM: Homo sapiens

<400> SEQUENCE: 88

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

```
Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

<210> SEQ ID NO 89
<211> LENGTH: 101
<212> TYPE: PRT
<213> ORGANISM: Homo sapiens

<400> SEQUENCE: 89

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 90
<211> LENGTH: 95
<212> TYPE: PRT
<213> ORGANISM: Homo sapiens

<400> SEQUENCE: 90

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95

<210> SEQ ID NO 91
<211> LENGTH: 95
<212> TYPE: PRT
<213> ORGANISM: Homo sapiens

<400> SEQUENCE: 91

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
```

```
                        50                  55                  60
Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro
                 85                  90                  95
```

<210> SEQ ID NO 92
<211> LENGTH: 95
<212> TYPE: PRT
<213> ORGANISM: Homo sapiens

<400> SEQUENCE: 92

```
Glu Ile Val Leu Thr Gln Ser Pro Asp Phe Gln Ser Val Thr Pro Lys
  1               5                  10                  15

Glu Lys Val Thr Ile Thr Cys Arg Ala Ser Gln Ser Ile Gly Ser Ser
                 20                  25                  30

Leu His Trp Tyr Gln Gln Lys Pro Asp Gln Ser Pro Lys Leu Leu Ile
             35                  40                  45

Lys Tyr Ala Ser Gln Ser Phe Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro
                 85                  90                  95
```

<210> SEQ ID NO 93
<211> LENGTH: 95
<212> TYPE: PRT
<213> ORGANISM: Homo sapiens

<400> SEQUENCE: 93

```
Asp Val Val Met Thr Gln Ser Pro Ala Phe Leu Ser Val Thr Pro Gly
  1               5                  10                  15

Glu Lys Val Thr Ile Thr Cys Gln Ala Ser Glu Gly Ile Gly Asn Tyr
                 20                  25                  30

Leu Tyr Trp Tyr Gln Gln Lys Pro Asp Gln Ala Pro Lys Leu Leu Ile
             35                  40                  45

Lys Tyr Ala Ser Gln Ser Ile Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gln Gln Gly Asn Lys His Pro
                 85                  90                  95
```

<210> SEQ ID NO 94
<211> LENGTH: 108
<212> TYPE: PRT
<213> ORGANISM: Mus musculus

<400> SEQUENCE: 94

```
Asp Ile Gln Met Thr Gln Ser Pro Ala Ser Leu Ser Ala Ser Val Gly
  1               5                  10                  15

Glu Thr Val Thr Ile Thr Cys Arg Ala Ser Gly Asn Ile His Asn Tyr
                 20                  25                  30

Leu Ala Trp Tyr Gln Gln Lys Gln Gly Lys Ser Pro Gln Leu Leu Val
             35                  40                  45

Tyr Tyr Thr Thr Thr Leu Ala Asp Gly Val Pro Ser Arg Phe Ser Gly
 50                  55                  60
```

-continued

```
Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys Arg
            100                 105

<210> SEQ ID NO 95
<211> LENGTH: 13
<212> TYPE: PRT
<213> ORGANISM: Homo sapiens

<400> SEQUENCE: 95

Trp Thr Phe Gly Gln Gly Thr Lys Val Glu Ile Lys Arg
1               5                   10

<210> SEQ ID NO 96
<211> LENGTH: 13
<212> TYPE: PRT
<213> ORGANISM: Homo sapiens

<400> SEQUENCE: 96

Tyr Thr Phe Gly Gln Gly Thr Lys Leu Glu Ile Lys Arg
1               5                   10

<210> SEQ ID NO 97
<211> LENGTH: 13
<212> TYPE: PRT
<213> ORGANISM: Homo sapiens

<400> SEQUENCE: 97

Phe Thr Phe Gly Pro Gly Thr Lys Val Asp Ile Lys Arg
1               5                   10

<210> SEQ ID NO 98
<211> LENGTH: 13
<212> TYPE: PRT
<213> ORGANISM: Homo sapiens

<400> SEQUENCE: 98

Leu Thr Phe Gly Gly Gly Thr Lys Val Glu Ile Lys Arg
1               5                   10

<210> SEQ ID NO 99
<211> LENGTH: 13
<212> TYPE: PRT
<213> ORGANISM: Homo sapiens

<400> SEQUENCE: 99

Ile Thr Phe Gly Gln Gly Thr Arg Leu Glu Ile Lys Arg
1               5                   10

<210> SEQ ID NO 100
<211> LENGTH: 116
<212> TYPE: PRT
<213> ORGANISM: Mus musculus

<400> SEQUENCE: 100

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30
```

```
Gly Val Asn Trp Val Arg Gln Pro Pro Gly Lys Gly Leu Glu Trp Leu
            35                  40                  45

Gly Met Ile Trp Gly Asp Gly Asn Thr Asp Tyr Asn Ser Ala Leu Lys
        50                  55                  60

Ser Arg Leu Ser Ile Ser Lys Asp Asn Ser Lys Ser Gln Val Phe Leu
65                  70                  75                  80

Lys Met Asn Ser Leu His Thr Asp Asp Thr Ala Arg Tyr Tyr Cys Ala
                85                  90                  95

Arg Glu Arg Asp Tyr Arg Leu Asp Tyr Trp Gly Gln Gly Thr Thr Leu
                100                 105                 110

Thr Val Ser Ser
            115

<210> SEQ ID NO 101
<211> LENGTH: 116
<212> TYPE: PRT
<213> ORGANISM: Homo sapiens

<400> SEQUENCE: 101

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Thr Val Ser Ser Asn
                20                  25                  30

Tyr Met Ser Trp Val Arg Gln Pro Pro Gly Lys Gly Leu Glu Trp Leu
            35                  40                  45

Gly Val Ile Tyr Ser Gly Gly Ser Thr Tyr Tyr Ala Asp Ser Val Lys
        50                  55                  60

Gly Arg Leu Ser Ile Ser Lys Asp Asn Ser Lys Ser Gln Val Phe Leu
65                  70                  75                  80

Lys Met Asn Ser Leu His Thr Asp Asp Thr Ala Arg Tyr Tyr Cys Ala
                85                  90                  95

Arg Glu Arg Asp Tyr Arg Leu Asp Tyr Trp Gly Gln Gly Thr Thr Leu
                100                 105                 110

Thr Val Ser Ser
            115

<210> SEQ ID NO 102
<211> LENGTH: 17
<212> TYPE: PRT
<213> ORGANISM: Homo sapiens

<400> SEQUENCE: 102

Ala Glu Tyr Phe Gln His Trp Gly Gln Gly Thr Leu Val Thr Val Ser
1               5                   10                  15

Ser

<210> SEQ ID NO 103
<211> LENGTH: 17
<212> TYPE: PRT
<213> ORGANISM: Homo sapiens

<400> SEQUENCE: 103

Tyr Trp Tyr Phe Asp Leu Trp Gly Arg Gly Thr Leu Val Thr Val Ser
1               5                   10                  15

Ser

<210> SEQ ID NO 104
<211> LENGTH: 15
```

```
<212> TYPE: PRT
<213> ORGANISM: Homo sapiens

<400> SEQUENCE: 104

Ala Phe Asp Val Trp Gly Gln Gly Thr Met Val Thr Val Ser Ser
1               5                   10                  15

<210> SEQ ID NO 105
<211> LENGTH: 15
<212> TYPE: PRT
<213> ORGANISM: Homo sapiens

<400> SEQUENCE: 105

Tyr Phe Asp Tyr Trp Gly Gln Gly Thr Leu Val Thr Val Ser Ser
1               5                   10                  15

<210> SEQ ID NO 106
<211> LENGTH: 16
<212> TYPE: PRT
<213> ORGANISM: Homo sapiens

<400> SEQUENCE: 106

Asn Trp Phe Asp Ser Trp Gly Gln Gly Thr Leu Val Thr Val Ser Ser
1               5                   10                  15

<210> SEQ ID NO 107
<211> LENGTH: 20
<212> TYPE: PRT
<213> ORGANISM: Homo sapiens

<400> SEQUENCE: 107

Tyr Tyr Tyr Asp Tyr Gly Met Asp Val Trp Gly Gln Gly Thr Thr Val
1               5                   10                  15

Thr Val Ser Ser
            20

<210> SEQ ID NO 108
<211> LENGTH: 1720
<212> TYPE: DNA
<213> ORGANISM: Homo sapiens
<220> FEATURE:
<221> NAME/KEY: CDS
<222> LOCATION: (119)..(829)
<220> FEATURE:
<221> NAME/KEY: CDS
<222> LOCATION: (914)..(1663)

<400> SEQUENCE: 108
```

| | | |
|---|---|---|
| gctgtcataa agttgtcacg gccgagactt atagtcgctt tgtttttatt ttttaatgta | | 60 |
| tttgtaacta gaattcgagc tcggtacccg gggatcctct agaggttgag gtgattt | | 118 |

| atg aaa aag aat atc gca ttt ctt ctt gca tct atg ttc gtt ttt tct | | 166 |
|---|---|---|
| Met Lys Lys Asn Ile Ala Phe Leu Leu Ala Ser Met Phe Val Phe Ser | | |
| 1               5                   10                  15 | | |

| att gct aca aac gcg tat gct gct atc cgt atg acc cag tcc ccg ttc | | 214 |
|---|---|---|
| Ile Ala Thr Asn Ala Tyr Ala Ala Ile Arg Met Thr Gln Ser Pro Phe | | |
|         20                  25                  30 | | |

| tct ctg tcc gct tct gtt ggt gac cgt gtt acc atc acc tgc cgt gct | | 262 |
|---|---|---|
| Ser Leu Ser Ala Ser Val Gly Asp Arg Val Thr Ile Thr Cys Arg Ala | | |
|     35                  40                  45 | | |

| tct ggt aac atc cac aac tac ctg gct tgg tac cag cag aaa ccg gct | | 310 |
|---|---|---|
| Ser Gly Asn Ile His Asn Tyr Leu Ala Trp Tyr Gln Gln Lys Pro Ala | | |
| 50                  55                  60 | | |

| aaa gct ccg aaa ctg ttc atc tac tac act act acc ctg gct gac ggt | | 358 |

```
Lys Ala Pro Lys Leu Phe Ile Tyr Tyr Thr Thr Thr Leu Ala Asp Gly
 65                  70                  75                  80 gtt ccg tct cgt ttc tcc ggt tct ggt tcc ggt act gac tac act ctg       406
Val Pro Ser Arg Phe Ser Gly Ser Gly Ser Gly Thr Asp Tyr Thr Leu
                     85                  90                  95 act atc tct tct ctg cag ccg gaa gac ttc gct act tac tac tgc cag       454
Thr Ile Ser Ser Leu Gln Pro Glu Asp Phe Ala Thr Tyr Tyr Cys Gln
                100                 105                 110 cac ttc tgg tcc act ccg cgt act ttc ggt ggt ggt act aaa gtt gaa       502
His Phe Trp Ser Thr Pro Arg Thr Phe Gly Gly Gly Thr Lys Val Glu
            115                 120                 125 atc aaa cgt acg gtg gct gca cca tct gtc ttc atc ttc ccg cca tct       550
Ile Lys Arg Thr Val Ala Ala Pro Ser Val Phe Ile Phe Pro Pro Ser
130                 135                 140 gat gag cag ttg aaa tct gga act gcc tct gtt gtg tgc ctg ctg aat       598
Asp Glu Gln Leu Lys Ser Gly Thr Ala Ser Val Val Cys Leu Leu Asn
145                 150                 155                 160 aac ttc tat ccc aga gag gcc aaa gta cag tgg aag gtg gat aac gcc       646
Asn Phe Tyr Pro Arg Glu Ala Lys Val Gln Trp Lys Val Asp Asn Ala
                165                 170                 175 ctc caa tcg ggt aac tcc cag gag agt gtc aca gag cag gac agc aag       694
Leu Gln Ser Gly Asn Ser Gln Glu Ser Val Thr Glu Gln Asp Ser Lys
            180                 185                 190 gac agc acc tac agc ctc agc agc acc ctg acg ctg agc aaa gca gac       742
Asp Ser Thr Tyr Ser Leu Ser Ser Thr Leu Thr Leu Ser Lys Ala Asp
        195                 200                 205 tac gag aaa cac aaa gtc tac gcc tgc gaa gtc acc cat cag ggc ctg       790
Tyr Glu Lys His Lys Val Tyr Ala Cys Glu Val Thr His Gln Gly Leu
210                 215                 220 agc tcg ccc gtc aca aag agc ttc aac agg gga gag tgt taagctgatc       839
Ser Ser Pro Val Thr Lys Ser Phe Asn Arg Gly Glu Cys
225                 230                 235 ctctacgccg acgcatcgt ggcccttgta cacaagttca cgtaaaaagg gtatctagag     899
gttgaggtga tttt atg aaa aag aat atc gca ttt ctt ctt gca tct atg      949
              Met Lys Lys Asn Ile Ala Phe Leu Leu Ala Ser Met
                  240                 245 ttc gtt ttt tct att gct aca aac gcg tac gct cag gtt cag ctg cag      997
Phe Val Phe Ser Ile Ala Thr Asn Ala Tyr Ala Gln Val Gln Leu Gln
250                 255                 260                 265 gaa tct ggt ccg ggt ctg gtt aaa ccg tct gaa act ctg tct ctg act      1045
Glu Ser Gly Pro Gly Leu Val Lys Pro Ser Glu Thr Leu Ser Leu Thr
                270                 275                 280 tgc act gtt tct ggt ggt tct gtt tct ggt tac ggt gtt aac tgg atc      1093
Cys Thr Val Ser Gly Gly Ser Val Ser Gly Tyr Gly Val Asn Trp Ile
                285                 290                 295 cgt cag ccg ccg ggt aaa ggt ctg gaa tgg atc ggt atg atc tgg ggt      1141
Arg Gln Pro Pro Gly Lys Gly Leu Glu Trp Ile Gly Met Ile Trp Gly
                300                 305                 310 gac ggt aac act gac tac aac tct tct ctg aaa tct cgt gtt act atc      1189
Asp Gly Asn Thr Asp Tyr Asn Ser Ser Leu Lys Ser Arg Val Thr Ile
            315                 320                 325 tct gtc gac act tct aaa aac cag ttc tct ctg aaa ctg tct tct gtt      1237
Ser Val Asp Thr Ser Lys Asn Gln Phe Ser Leu Lys Leu Ser Ser Val
330                 335                 340                 345 act gct gct gac act gct gtt tac tac tgc gct cgt gaa cgt gac tac      1285
Thr Ala Ala Asp Thr Ala Val Tyr Tyr Cys Ala Arg Glu Arg Asp Tyr
                350                 355                 360 cgt ctg gac tac tgg ggt cag ggt act ctg gtt act gtt tct tct gcc      1333
Arg Leu Asp Tyr Trp Gly Gln Gly Thr Leu Val Thr Val Ser Ser Ala
```

-continued

```
                   365                 370                 375
tcc acc aag ggc cca tcg gtc ttc ccc ctg gca ccc tcc tcc aag agc      1381
Ser Thr Lys Gly Pro Ser Val Phe Pro Leu Ala Pro Ser Ser Lys Ser
            380                 385                 390 acc tct ggg ggc aca gcg gcc ctg ggc tgc ctg gtc aag gac tac ttc      1429
Thr Ser Gly Gly Thr Ala Ala Leu Gly Cys Leu Val Lys Asp Tyr Phe
    395                 400                 405 ccc gaa ccg gtg acg gtg tcg tgg aac tca ggc gcc ctg acc agc ggc      1477
Pro Glu Pro Val Thr Val Ser Trp Asn Ser Gly Ala Leu Thr Ser Gly
410                 415                 420                 425 gtg cac acc ttc ccg gct gtc cta cag tcc tca gga ctc tac tcc ctc      1525
Val His Thr Phe Pro Ala Val Leu Gln Ser Ser Gly Leu Tyr Ser Leu
                430                 435                 440 agc agc gtg gtg acc gtg ccc tcc agc agc ttg ggc acc cag acc tac      1573
Ser Ser Val Val Thr Val Pro Ser Ser Ser Leu Gly Thr Gln Thr Tyr
            445                 450                 455 atc tgc aac gtg aat cac aag ccc agc aac acc aag gtc gac aag aaa      1621
Ile Cys Asn Val Asn His Lys Pro Ser Asn Thr Lys Val Asp Lys Lys
    460                 465                 470 gtt gag ccc aaa tct tgt gac aaa act cac aca tgc gcc gcg              1663
Val Glu Pro Lys Ser Cys Asp Lys Thr His Thr Cys Ala Ala
475                 480                 485 tgacgcggca tgcgacggcc ctagagtccc taacgctcgg ttgccgccgg gcgtttt       1720
```

<210> SEQ ID NO 109
<211> LENGTH: 237
<212> TYPE: PRT
<213> ORGANISM: Homo sapiens

<400> SEQUENCE: 109

```
Met Lys Lys Asn Ile Ala Phe Leu Leu Ala Ser Met Phe Val Phe Ser
1               5                   10                  15

Ile Ala Thr Asn Ala Tyr Ala Ala Ile Arg Met Thr Gln Ser Pro Phe
            20                  25                  30

Ser Leu Ser Ala Ser Val Gly Asp Arg Val Thr Ile Thr Cys Arg Ala
        35                  40                  45

Ser Gly Asn Ile His Asn Tyr Leu Ala Trp Tyr Gln Gln Lys Pro Ala
    50                  55                  60

Lys Ala Pro Lys Leu Phe Ile Tyr Tyr Thr Thr Thr Leu Ala Asp Gly
65                  70                  75                  80

Val Pro Ser Arg Phe Ser Gly Ser Gly Ser Gly Thr Asp Tyr Thr Leu
                85                  90                  95

Thr Ile Ser Ser Leu Gln Pro Glu Asp Phe Ala Thr Tyr Tyr Cys Gln
            100                 105                 110

His Phe Trp Ser Thr Pro Arg Thr Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205
```

```
Tyr Glu Lys His Lys Val Tyr Ala Cys Glu Val Thr His Gln Gly Leu
    210                 215                 220
Ser Ser Pro Val Thr Lys Ser Phe Asn Arg Gly Glu Cys
225                 230                 235

<210> SEQ ID NO 110
<211> LENGTH: 250
<212> TYPE: PRT
<213> ORGANISM: Homo sapiens

<400> SEQUENCE: 110

Met Lys Lys Asn Ile Ala Phe Leu Leu Ala Ser Met Phe Val Phe Ser
1               5                   10                  15
Ile Ala Thr Asn Ala Tyr Ala Gln Val Gln Leu Gln Glu Ser Gly Pro
            20                  25                  30
Gly Leu Val Lys Pro Ser Glu Thr Leu Ser Leu Thr Cys Thr Val Ser
        35                  40                  45
Gly Gly Ser Val Ser Gly Tyr Gly Val Asn Trp Ile Arg Gln Pro Pro
    50                  55                  60
Gly Lys Gly Leu Glu Trp Ile Gly Met Ile Trp Gly Asp Gly Asn Thr
65                  70                  75                  80
Asp Tyr Asn Ser Ser Leu Lys Ser Arg Val Thr Ile Ser Val Asp Thr
                85                  90                  95
Ser Lys Asn Gln Phe Ser Leu Lys Leu Ser Ser Val Thr Ala Ala Asp
            100                 105                 110
Thr Ala Val Tyr Tyr Cys Ala Arg Glu Arg Asp Tyr Arg Leu Asp Tyr
        115                 120                 125
Trp Gly Gln Gly Thr Leu Val Thr Val Ser Ser Ala Ser Thr Lys Gly
    130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Ser Leu Gly Thr Gln Thr Tyr Ile Cys Asn Val
    210                 215                 220
Asn His Lys Pro Ser Asn Thr Lys Val Asp Lys Lys Val Glu Pro Lys
225                 230                 235                 240
Ser Cys Asp Lys Thr His Thr Cys Ala Ala
                245                 250

<210> SEQ ID NO 111
<211> LENGTH: 108
<212> TYPE: PRT
<213> ORGANISM: Homo sapiens

<400> SEQUENCE: 111

Ala Ile Arg Met Thr Gln Ser Pro Phe Ser Leu Ser Ala Ser Val Gly
1               5                   10                  15
Asp Arg Val Thr Ile Thr Cys Arg Ala Ser Gly Asn Ile His Asn Tyr
            20                  25                  30
Leu Ala Trp Tyr Gln Gln Lys Pro Ala Lys Ala Pro Lys Leu Phe Ile
        35                  40                  45
```

```
Tyr Tyr Thr Thr Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Ser Thr Pro Arg
                 85                  90                  95

Thr Phe Gly Gly Gly Thr Lys Val Glu Ile Lys Arg
             100                 105
```

<210> SEQ ID NO 112
<211> LENGTH: 116
<212> TYPE: PRT
<213> ORGANISM: Homo sapiens

<400> SEQUENCE: 112

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Gly Tyr
                20                  25                  30

Gly Val Asn Trp Ile Arg Gln Pro Pro Gly Lys Gly Leu Glu Trp Ile
             35                  40                  45

Gly Met Ile Trp Gly Asp Gly Asn Thr Asp Tyr Asn Ser Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Glu Arg Asp Tyr Arg Leu Asp Tyr Trp Gly Gln Gly Thr Leu Val
             100                 105                 110

Thr Val Ser Ser
        115
```

<210> SEQ ID NO 113
<211> LENGTH: 112
<212> TYPE: PRT
<213> ORGANISM: Mus musculus

<400> SEQUENCE: 113

```
Asp Ile Glu Leu Thr Gln Ser Pro Ala Ser Leu Ala Val Ser Leu Gly
 1               5                  10                  15

Gln Arg Ala Thr Ile Ser Cys Arg Ala Ser Glu Ser Val Glu Tyr Tyr
                20                  25                  30

Val Thr Ser Leu Met Gln Trp Tyr Gln Gln Lys Pro Gly Gln Pro Pro
             35                  40                  45

Lys Leu Leu Ile Phe Ala Ala Ser Asn Val Glu Ser Gly Val Pro Ala
 50                  55                  60

Arg Phe Ser Gly Ser Gly Ser Gly Thr Asn Phe Ser Leu Asn Ile His
 65                  70                  75                  80

Pro Val Asp Glu Asp Asp Val Ala Met Tyr Phe Cys Gln Gln Ser Arg
                 85                  90                  95

Lys Val Pro Tyr Thr Phe Gly Gly Gly Thr Lys Leu Glu Ile Lys Arg
             100                 105                 110
```

<210> SEQ ID NO 114
<211> LENGTH: 120
<212> TYPE: PRT
<213> ORGANISM: Mus musculus -continued

<400> SEQUENCE: 114

Glu Val Lys Leu Gln Gln Ser Gly Pro Gly Leu Val Thr Pro Ser Gln
1               5                   10                  15

Ser Leu Ser Ile Thr Cys Thr Val Ser Gly Phe Ser Leu Ser Asp Tyr
            20                  25                  30

Gly Val His Trp Val Arg Gln Ser Pro Gly Gln Gly Leu Glu Trp Leu
        35                  40                  45

Gly Val Ile Trp Ala Gly Gly Thr Asn Tyr Asn Ser Ala Leu Met
    50                  55                  60

Ser Arg Lys Ser Ile Ser Lys Asp Asn Ser Lys Ser Gln Val Phe Leu
65                  70                  75                  80

Lys Met Asn Ser Leu Gln Ala Asp Asp Thr Ala Val Tyr Tyr Cys Ala
                85                  90                  95

Arg Asp Lys Gly Tyr Ser Tyr Tyr Ser Met Asp Tyr Trp Gly Gln
            100                 105                 110

Gly Thr Ser Val Thr Val Ser Ser
        115                 120

<210> SEQ ID NO 115
<211> LENGTH: 112
<212> TYPE: PRT
<213> ORGANISM: Homo sapiens

<400> SEQUENCE: 115

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Val Thr Ser Leu Met Ala Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asn Phe Ser Leu Thr Ile Ser
65                  70                  75                  80

Ser Leu Gln Ala Glu Asp Val Ala Val Tyr Tyr Cys Gln Gln Ser Arg
                85                  90                  95

Lys Val Pro Tyr Thr Phe Gly Gln Gly Thr Lys Leu Glu Ile Lys Arg
            100                 105                 110

<210> SEQ ID NO 116
<211> LENGTH: 120
<212> TYPE: PRT
<213> ORGANISM: Homo sapiens

<400> SEQUENCE: 116

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Asp Tyr
            20                  25                  30

Gly Val His Trp Val Arg Gln Ala Pro Gly Lys Gly Leu Glu Trp Val
        35                  40                  45

Ser Ala Ile Trp Ala Gly Gly Thr Asn Tyr Ala Ser Ser Val Met
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala

```
                    85                  90                  95
Arg Asp Lys Gly Tyr Ser Tyr Tyr Ser Met Asp Tyr Trp Gly Gln
            100                 105                 110
Gly Thr Leu Val Thr Val Ser Ser
        115                 120

<210> SEQ ID NO 117
<211> LENGTH: 112
<212> TYPE: PRT
<213> ORGANISM: Mus musculus

<400> SEQUENCE: 117

Asp Ile Val Leu Thr Gln Ser Pro Val Ser Leu Ala Val Ser Val Gly
1               5                   10                  15
Gln Arg Ala Thr Ile Ser Cys Lys Ala Ser Gln Ser Val Asp Phe Asp
            20                  25                  30
Gly Glu Ser Tyr Met Asn Trp Tyr Gln Gln Lys Pro Gly Gln Pro Pro
        35                  40                  45
Lys Leu Leu Ile Tyr Val Val Ser Asn Leu Glu Ser Gly Ile Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln Gln Ser Asn
                85                  90                  95
Glu Asp Pro Leu Thr Phe Gly Ala Gly Thr Asn Leu Glu Leu Lys Arg
            100                 105                 110

<210> SEQ ID NO 118
<211> LENGTH: 112
<212> TYPE: PRT
<213> ORGANISM: Homo sapiens

<400> SEQUENCE: 118

Asp Ile Val Met Thr Gln Thr Pro Leu Ser Leu Ser Val Thr Pro Gly
1               5                   10                  15
Gln Pro Ala Ser Ile Ser Cys Lys Ala Ser Gln Ser Val Asp Phe Asp
            20                  25                  30
Gly Glu Ser Tyr Met Asn Trp Tyr Leu Gln Lys Pro Gly Gln Pro Pro
        35                  40                  45
Gln Leu Leu Ile Tyr Val Val Ser Asn Leu Glu Ser Gly Val Pro Asp
    50                  55                  60
Arg Phe Ser Gly Ser Gly Ser Gly Thr Asp Phe Thr Leu Lys Ile Ser
65                  70                  75                  80
Arg Val Glu Ala Glu Asp Val Gly Val Tyr Tyr Cys Gln Gln Ser Asn
                85                  90                  95
Glu Asp Pro Leu Thr Phe Gly Gly Gly Tyr Lys Val Glu Ile Lys Arg
            100                 105                 110

<210> SEQ ID NO 119
<211> LENGTH: 117
<212> TYPE: PRT
<213> ORGANISM: Mus musculus

<400> SEQUENCE: 119

Glu Val Gln Leu Gln Gln Ser Gly Pro Glu Leu Val Lys Pro Gly Ala
1               5                   10                  15
Ser Met Lys Ile Ser Cys Lys Val Ser Gly Tyr Ser Phe Thr Asp His
            20                  25                  30
```

-continued

Thr Met Asn Trp Val Lys Gln Ser His Gly Lys Asn Leu Glu Leu Ile
            35                  40                  45

Gly Leu Ile Asn Pro Phe Asn Gly Asp Ala Thr Tyr Lys Gln Lys Phe
 50                  55                  60

Thr Gly Lys Ala Thr Leu Thr Val Asp Arg Ser Ser Thr Ala Phe
65                  70                  75                  80

Met Glu Leu Leu Ser Leu Thr Ser Glu Asp Ser Ala Val Tyr Tyr Cys
                85                  90                  95

Ala Arg Tyr Gly Asn Tyr Ala Met Asp Tyr Trp Gly Gln Gly Thr Ser
                100                 105                 110

Val Thr Val Ser Ser
        115

<210> SEQ ID NO 120
<211> LENGTH: 117
<212> TYPE: PRT
<213> ORGANISM: Homo sapiens

<400> SEQUENCE: 120

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp His
            20                  25                  30

Thr Met Asn Trp Val Gln Gln Ala Pro Gly Lys Gly Leu Glu Trp Met
            35                  40                  45

Gly Leu Ile Asn Pro Phe Asn Gly Asp Ala Thr Tyr Lys Gln Lys Phe
 50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Asn Tyr Ala Met Asp Tyr Trp Gly Gln Gly Thr Thr
                100                 105                 110

Val Thr Val Ser Ser
        115

<210> SEQ ID NO 121
<211> LENGTH: 111
<212> TYPE: PRT
<213> ORGANISM: Mus musculus

<400> SEQUENCE: 121

Val Leu Thr Gln Thr Pro Leu Ser Leu Pro Val Ser Leu Gly Asp Gln
1               5                   10                  15

Ala Ser Ile Ser Cys Arg Ser Ser Gln Ser Leu Glu His Asn Asn Gly
            20                  25                  30

Asn Thr Tyr Leu Asn Trp Tyr Leu Gln Lys Pro Gly Gln Ser Pro Gln
            35                  40                  45

Leu Leu Ile Tyr Arg Val Ser Asn Arg Phe Ser Gly Leu Asp Arg
 50                  55                  60

Phe Ser Gly Ser Gly Ser Gly Thr Asp Phe Thr Leu Lys Ile Ser Arg
65                  70                  75                  80

Val Glu Ala Glu Asp Leu Gly Val Tyr Phe Cys Leu Gln Val Thr His
                85                  90                  95

Val Pro Phe Thr Phe Gly Ser Gly Thr Lys Leu Glu Ile Lys Arg
                100                 105                 110

<210> SEQ ID NO 122
<211> LENGTH: 113
<212> TYPE: PRT
<213> ORGANISM: Homo sapiens

<400> SEQUENCE: 122

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu His Asn
            20                  25                  30

Asn Gly Asn Thr Tyr Leu Asn Trp Phe Gln Gln Arg Pro Gly Gln Ser
        35                  40                  45

Pro Arg Arg Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Phe Thr Phe Gly Pro Gly Thr Lys Val Asp Ile Lys
            100                 105                 110

Arg

<210> SEQ ID NO 123
<211> LENGTH: 119
<212> TYPE: PRT
<213> ORGANISM: Mus musculus

<400> SEQUENCE: 123

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Arg Phe Ser Ser Tyr
            20                  25                  30

Asn Met His Trp Val Lys Gln Thr Pro Gly Gln Gly Leu Glu Trp Ile
        35                  40                  45

Gly Ala Ile Tyr Pro Arg Ser Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Gly Ser Leu Thr Ser Glu Asp Ser Ala Val Tyr Tyr Cys
                85                  90                  95

Val Arg Ser Tyr Asp Tyr Asp Ala Pro Phe Ala Phe Trp Gly Gln Gly
            100                 105                 110

Thr Leu Val Thr Val Ser Ala
        115

<210> SEQ ID NO 124
<211> LENGTH: 119
<212> TYPE: PRT
<213> ORGANISM: Homo sapiens

<400> SEQUENCE: 124

Glu Val Gln Leu Leu Gln Ser Ala Ala Glu Val Lys Arg Pro Gly Glu
1               5                   10                  15

Ser Leu Arg Ile Ser Cys Lys Thr Ser Gly Tyr Ser Phe Thr Ser Tyr
            20                  25                  30

Asn Met His Trp Val Arg Gln Met Pro Gly Lys Glu Leu Glu Trp Met

-continued

```
                35                    40                      45
Gly Ala Ile Tyr Pro Arg Ser Gly Asp Thr Ser Tyr Asn Pro Ser Phe
        50                  55                  60

Gln Gly His Val Thr Ile Ser Ala Asp Ser Ser Ser Ser Thr Ala Tyr
65              70                  75                  80

Leu Gln Trp Ser Ser Leu Lys Ala Ser Asp Ala Ala Met Tyr Tyr Cys
                85                  90                  95

Val Arg Ser Tyr Asp Tyr Asp Ala Pro Phe Ala Phe Trp Gly Gln Gly
                100                 105                 110

Thr Leu Val Thr Val Ser Ser
            115
```